(12) United States Patent
Andreas et al.

(10) Patent No.: US 9,883,957 B2
(45) Date of Patent: Feb. 6, 2018

(54) APPARATUS AND METHODS FOR DEPLOYMENT OF LINKED PROSTHETIC SEGMENTS

(71) Applicant: J.W. Medical Systems Ltd., Weihai Shandong (CN)

(72) Inventors: Bernard Andreas, Redwood City, CA (US); Sunmi Chew, San Jose, CA (US); Jeremy Dittmer, Stanford, CA (US); Jeff Grainger, Portola Valley, CA (US); Stephen Kao, Sunnyvale, CA (US); David Lowe, Redwood City, CA (US); Bryan Mao, San Francisco, CA (US); Stephen Olson, Los Altos, CA (US); David Snow, San Carlos, CA (US); Craig Welk, Tracy, CA (US)

(73) Assignee: J.W. Medical Systems Ltd., Weihai, Shandong (CN)

( * ) Notice: Subject to any disclaimer, the term of this patent is extended or adjusted under 35 U.S.C. 154(b) by 0 days.

(21) Appl. No.: 14/183,323

(22) Filed: Feb. 18, 2014

(65) Prior Publication Data
US 2014/0236282 A1 Aug. 21, 2014

Related U.S. Application Data

(62) Division of application No. 11/687,885, filed on Mar. 19, 2007, now Pat. No. 8,652,198.
(Continued)

(51) Int. Cl.
*A61F 2/89* (2013.01)
*A61B 17/12* (2006.01)
(Continued)

(52) U.S. Cl.
CPC .......... *A61F 2/89* (2013.01); *A61B 17/12022* (2013.01); *A61F 2/91* (2013.01);
(Continued)

(58) Field of Classification Search
CPC ................ A61F 2/915; A61F 2002/826; A61F 2002/075; A61F 2002/828; A61F 2/89;
(Continued)

(56) References Cited

U.S. PATENT DOCUMENTS 2,835,501 A 5/1958 Chamberlin et al.
4,069,825 A 1/1978 Akiyama
(Continued)

FOREIGN PATENT DOCUMENTS

CN 1856280 A 1/2006
CN 104068951 1/2014
(Continued)

OTHER PUBLICATIONS

Chu et al., "Preparation of Thermo-Responsive Core-Shell Microcapsules with a Porous Membrane and Poly(N-isopropylacrylamide) Gates," J Membrane Sci, Oct. 15, 2001; 192(1-2):27-39.
(Continued)

*Primary Examiner* — Katherine Rodjom
(74) *Attorney, Agent, or Firm* — Kilpatrick Townsend & Stockton LLP

(57) ABSTRACT

A luminal prosthesis comprises a plurality of radially expandable prosthetic stent segments arranged axially. Two or more of the prosthetic stent segments are separable upon expansion from the remaining prosthetic stent segments and a coupling structure connects at least some of the adjacent prosthetic stent segments to each other. The coupling structure permits a first group of the adjacent prosthetic stent segments to separate from a second group of the prosthetic (Continued)

stent segments upon differential radial expansion of the first group relative to the second group and the coupling structure maintains or forms an attachment between the adjacent prosthetic stent segments in the first group which have been expanded together. A delivery system and methods for deploying the multiple coupled prosthetic stent segments are also disclosed.

11 Claims, 22 Drawing Sheets

Related U.S. Application Data

(60) Provisional application No. 60/784,309, filed on Mar. 20, 2006.

(51) Int. Cl.
| | | |
|---|---|---|
| *A61F 2/91* | (2013.01) | |
| *A61F 2/915* | (2013.01) | |
| *A61F 2/95* | (2013.01) | |
| *A61F 2/958* | (2013.01) | |
| A61F 2/852 | (2013.01) | |
| A61F 2/30 | (2006.01) | |
| A61F 2/82 | (2013.01) | |
| A61F 2/966 | (2013.01) | |

(52) U.S. Cl.
CPC ............... *A61F 2/915* (2013.01); *A61F 2/95* (2013.01); *A61F 2/958* (2013.01); *A61B 2017/1205* (2013.01); *A61B 2017/12068* (2013.01); *A61F 2/852* (2013.01); *A61F 2002/30329* (2013.01); *A61F 2002/30545* (2013.01); *A61F 2002/30599* (2013.01); *A61F 2002/826* (2013.01); *A61F 2002/828* (2013.01); *A61F 2002/91508* (2013.01); *A61F 2002/91525* (2013.01); *A61F 2002/91533* (2013.01); *A61F 2002/91541* (2013.01); *A61F 2002/91558* (2013.01); *A61F 2002/91575* (2013.01); *A61F 2002/91591* (2013.01); *A61F 2002/9665* (2013.01); *A61F 2220/005* (2013.01); *A61F 2220/0008* (2013.01); *A61F 2220/0025* (2013.01); *A61F 2220/0058* (2013.01); *A61F 2230/0013* (2013.01); *A61F 2230/0067* (2013.01); *A61F 2250/001* (2013.01); *A61F 2250/0063* (2013.01); *A61F 2250/0071* (2013.01)

(58) Field of Classification Search
CPC .... A61F 2002/91583; A61F 2002/9511; A61F 2002/9155
USPC .............................. 623/1.11, 1.16, 1.12, 1.23
See application file for complete search history.

(56) References Cited

U.S. PATENT DOCUMENTS

| | | |
|---|---|---|
| 4,468,224 A | 8/1984 | Enzmann et al. |
| 4,512,338 A | 4/1985 | Balko |
| 4,564,014 A | 1/1986 | Fogarty et al. |
| 4,580,568 A | 4/1986 | Gianturco |
| 4,681,110 A | 7/1987 | Wiktor |
| 4,690,684 A | 9/1987 | McGreevy et al. |
| 4,733,665 A | 3/1988 | Palmaz |
| 4,739,762 A | 4/1988 | Palmaz |
| 4,748,982 A | 6/1988 | Horzewski et al. |
| 4,762,129 A | 8/1988 | Bonzel |
| 4,770,176 A | 9/1988 | McGreevy et al. |
| 4,775,337 A | 10/1988 | Van Wagener et al. |
| 4,776,337 A | 10/1988 | Palmaz |
| 4,886,062 A | 12/1989 | Wiktor |
| 4,891,225 A | 1/1990 | Langer et al. |
| 4,950,227 A | 8/1990 | Savin et al. |
| 4,988,356 A | 1/1991 | Crittenden et al. |
| 4,994,066 A | 2/1991 | Voss |
| 4,994,069 A | 2/1991 | Ritchart et al. |
| 4,994,298 A | 2/1991 | Yasuda |
| 5,013,318 A | 5/1991 | Spranza, III |
| 5,026,377 A | 6/1991 | Burton et al. |
| 5,035,706 A | 7/1991 | Giantureo et al. |
| 5,040,548 A | 8/1991 | Yock |
| 5,061,273 A | 10/1991 | Yock |
| 5,064,435 A | 11/1991 | Porter |
| 5,092,877 A | 3/1992 | Pinchuk |
| 5,102,417 A | 4/1992 | Palmaz |
| 5,104,404 A | 4/1992 | Wolff |
| 5,122,154 A | 6/1992 | Rhodes |
| 5,135,535 A | 8/1992 | Kramer |
| 5,158,548 A | 10/1992 | Lau et al. |
| 5,171,222 A | 12/1992 | Euteneuer et al. |
| 5,192,297 A | 3/1993 | Hull |
| 5,195,984 A | 3/1993 | Schatz |
| 5,201,757 A | 4/1993 | Heyn et al. |
| 5,217,495 A | 6/1993 | Kaplan et al. |
| 5,219,355 A | 6/1993 | Parodi et al. |
| 5,226,913 A | 7/1993 | Pinchuk |
| 5,246,421 A | 9/1993 | Saab |
| 5,261,887 A | 11/1993 | Walker |
| 5,273,536 A | 12/1993 | Savas |
| 5,275,365 A | 1/1994 | Gerbel et al. |
| 5,282,823 A | 2/1994 | Schwartz et al. |
| 5,282,824 A * | 2/1994 | Gianturco ................. A61F 2/07 606/191 |
| 5,300,085 A | 4/1994 | Yock |
| 5,312,415 A | 5/1994 | Palermo |
| 5,328,469 A | 7/1994 | Coletti |
| 5,334,187 A | 8/1994 | Fischell et al. |
| 5,391,172 A | 2/1995 | Williams et al. |
| 5,421,955 A | 6/1995 | Lau et al. |
| 5,443,498 A | 8/1995 | Fontaine |
| 5,445,646 A | 8/1995 | Euteneuer et al. |
| 5,456,713 A | 10/1995 | Chuter |
| 5,458,615 A | 10/1995 | Klemm et al. |
| 5,470,315 A | 11/1995 | Adams |
| 5,478,349 A | 12/1995 | Nicholas |
| 5,484,444 A | 1/1996 | Braunschweiler et al. |
| 5,490,837 A | 2/1996 | Blaeser et al. |
| 5,496,346 A | 3/1996 | Horzewski et al. |
| 5,501,227 A | 3/1996 | Yock |
| 5,507,768 A | 4/1996 | Lau et al. |
| 5,507,771 A | 4/1996 | Gianturco |
| 5,514,093 A | 5/1996 | Ellis et al. |
| 5,514,154 A | 5/1996 | Lau et al. |
| 5,522,882 A | 6/1996 | Gaterud et al. |
| 5,527,354 A | 6/1996 | Fontaine et al. |
| 5,531,735 A | 7/1996 | Thompson |
| 5,533,968 A | 7/1996 | Muni et al. |
| 5,534,007 A | 7/1996 | St. Germain et al. |
| 5,545,209 A | 8/1996 | Roberts et al. |
| 5,549,551 A | 8/1996 | Peacock, III et al. |
| 5,549,563 A | 8/1996 | Kronner |
| 5,549,635 A | 8/1996 | Solar |
| 5,554,181 A | 9/1996 | Das |
| 5,562,725 A | 10/1996 | Schmitt et al. |
| 5,566,961 A | 10/1996 | Snell et al. |
| 5,571,086 A | 11/1996 | Kaplan et al. |
| 5,588,659 A | 12/1996 | Boes et al. |
| 5,591,195 A | 1/1997 | Taheri et al. |
| 5,593,412 A | 1/1997 | Martinez et al. |
| 5,607,444 A | 3/1997 | Lam |
| 5,607,463 A | 3/1997 | Schwartz et al. |
| 5,628,755 A | 5/1997 | Heller et al. |
| 5,628,775 A | 5/1997 | Jackson et al. |
| 5,634,928 A | 6/1997 | Fischell et al. |
| 5,639,274 A | 6/1997 | Fischell et al. |
| 5,662,675 A | 9/1997 | Stockert et al. |
| 5,662,703 A | 9/1997 | Yurek et al. |
| 5,670,161 A | 9/1997 | Healy et al. |

(56) References Cited

U.S. PATENT DOCUMENTS

| | | | |
|---|---|---|---|
| 5,676,654 A | 10/1997 | Ellis et al. | |
| 5,683,451 A | 11/1997 | Lenker et al. | |
| 5,690,644 A | 11/1997 | Yurek et al. | |
| 5,693,085 A | 12/1997 | Buirge et al. | |
| 5,697,948 A | 12/1997 | Marin et al. | |
| 5,697,971 A | 12/1997 | Fischell et al. | |
| 5,702,418 A | 12/1997 | Ravenscroft | |
| 5,702,419 A | 12/1997 | Berry et al. | |
| 5,709,701 A | 1/1998 | Parodi | |
| 5,716,393 A | 2/1998 | Lindenberg et al. | |
| 5,722,669 A | 3/1998 | Shimizu et al. | |
| 5,723,003 A | 3/1998 | Winston et al. | |
| 5,735,869 A | 4/1998 | Fernandez-Aceytuno | |
| 5,741,323 A | 4/1998 | Pathak et al. | |
| 5,749,848 A | 5/1998 | Jang et al. | |
| 5,749,890 A | 5/1998 | Shaknovich | |
| 5,749,921 A | 5/1998 | Lenker et al. | |
| 5,755,697 A | 5/1998 | Jones et al. | |
| 5,755,772 A | 5/1998 | Evans et al. | |
| 5,755,776 A | 5/1998 | Al-Saadon | |
| 5,755,781 A * | 5/1998 | Jayaraman | A61F 2/91 623/1.16 |
| 5,769,882 A | 6/1998 | Fogarty et al. | |
| 5,772,669 A | 6/1998 | Vrba | |
| 5,776,141 A | 7/1998 | Klein et al. | |
| 5,792,144 A | 8/1998 | Fischell et al. | |
| 5,797,951 A | 8/1998 | Mueller et al. | |
| 5,800,519 A | 9/1998 | Sandock | |
| 5,806,943 A | 9/1998 | Dell et al. | |
| 5,807,398 A | 9/1998 | Shaknovich | |
| 5,824,040 A | 10/1998 | Cox et al. | |
| 5,824,041 A | 10/1998 | Lenker et al. | |
| 5,833,694 A | 11/1998 | Poncet | |
| 5,836,964 A | 11/1998 | Richter et al. | |
| 5,843,090 A | 12/1998 | Schuetz | |
| 5,843,092 A | 12/1998 | Heller et al. | |
| 5,855,563 A | 1/1999 | Kaplan et al. | |
| 5,858,556 A | 1/1999 | Eckert et al. | |
| 5,870,381 A | 2/1999 | Kawasaki et al. | |
| 5,879,370 A | 3/1999 | Fischell et al. | |
| 5,891,190 A | 4/1999 | Boneau | |
| 5,895,398 A | 4/1999 | Wensel et al. | |
| 5,899,935 A | 5/1999 | Ding | |
| 5,902,332 A | 5/1999 | Schatz | |
| 5,919,175 A | 7/1999 | Sirhan | |
| 5,921,971 A | 7/1999 | Agro et al. | |
| 5,922,020 A | 7/1999 | Klein et al. | |
| 5,938,396 A | 8/1999 | Audet | |
| 5,941,869 A | 8/1999 | Patterson et al. | |
| 5,951,585 A | 9/1999 | Cathcart et al. | |
| 5,961,536 A | 10/1999 | Mickley et al. | |
| 5,965,879 A | 10/1999 | Leviton | |
| 5,968,069 A | 10/1999 | Dusbabek et al. | |
| 5,972,027 A | 10/1999 | Johnson | |
| 5,976,107 A | 11/1999 | Mertens et al. | |
| 5,976,155 A | 11/1999 | Foreman et al. | |
| 5,980,484 A | 11/1999 | Ressemann et al. | |
| 5,980,486 A | 11/1999 | Enger | |
| 5,980,514 A | 11/1999 | Kupiecki et al. | |
| 5,980,552 A | 11/1999 | Pinchasik et al. | |
| 5,984,957 A | 11/1999 | Laptewicz, Jr. et al. | |
| 5,989,280 A | 11/1999 | Euteneuer et al. | |
| 5,993,484 A | 11/1999 | Shmulewitz | |
| 5,997,563 A | 12/1999 | Kretzers et al. | |
| 6,004,328 A | 12/1999 | Solar | |
| 6,007,517 A | 12/1999 | Anderson | |
| 6,010,530 A | 1/2000 | Goicoechea | |
| 6,022,359 A | 2/2000 | Frantzen | |
| 6,022,374 A | 2/2000 | Imran | |
| 6,027,519 A | 2/2000 | Stanford | |
| 6,033,434 A | 3/2000 | Borghi | |
| 6,036,725 A | 3/2000 | Avellanet | |
| 6,039,721 A | 3/2000 | Johnson et al. | |
| 6,042,589 A | 3/2000 | Marianne | |
| 6,050,999 A | 4/2000 | Paraschac et al. | |
| 6,056,722 A | 5/2000 | Jayaraman | |
| 6,063,111 A | 5/2000 | Hieshima et al. | |
| 6,066,155 A | 5/2000 | Amann et al. | |
| 6,068,655 A | 5/2000 | Seguin et al. | |
| 6,070,589 A | 6/2000 | Keith et al. | |
| 6,090,063 A | 7/2000 | Makower et al. | |
| 6,090,136 A | 7/2000 | McDonald et al. | |
| 6,102,942 A | 8/2000 | Ahari | |
| 6,106,530 A | 8/2000 | Harada | |
| RE36,857 E | 9/2000 | Euteneuer et al. | |
| 6,113,129 A | 9/2000 | Marques et al. | |
| 6,120,477 A | 9/2000 | Campbell et al. | |
| 6,120,522 A | 9/2000 | Vrba et al. | |
| 6,123,712 A | 9/2000 | Di Caprio et al. | |
| 6,123,723 A | 9/2000 | Konya et al. | |
| 6,126,685 A | 10/2000 | Lenker et al. | |
| 6,129,756 A | 10/2000 | Kugler | |
| 6,132,460 A | 10/2000 | Thompson | |
| 6,139,572 A | 10/2000 | Campbell et al. | |
| 6,143,016 A | 11/2000 | Bleam et al. | |
| 6,165,167 A | 12/2000 | Delaloye | |
| 6,165,210 A | 12/2000 | Lau et al. | |
| 6,171,334 B1 | 1/2001 | Cox | |
| 6,179,878 B1 | 1/2001 | Duering | |
| 6,183,509 B1 | 2/2001 | Dibie | |
| 6,187,034 B1 | 2/2001 | Frantzen | |
| 6,190,402 B1 | 2/2001 | Horton et al. | |
| 6,196,995 B1 | 3/2001 | Fagan | |
| 6,200,337 B1 | 3/2001 | Moriuchi et al. | |
| 6,217,585 B1 | 4/2001 | Houser et al. | |
| 6,238,991 B1 | 5/2001 | Suzuki | |
| 6,241,691 B1 | 6/2001 | Ferrera et al. | |
| 6,241,758 B1 | 6/2001 | Cox | |
| 6,248,122 B1 | 6/2001 | Klumb et al. | |
| 6,251,132 B1 | 6/2001 | Ravenscroft et al. | |
| 6,251,134 B1 | 6/2001 | Alt et al. | |
| 6,254,612 B1 | 7/2001 | Hieshima | |
| 6,254,628 B1 | 7/2001 | Wallace et al. | |
| 6,258,117 B1 | 7/2001 | Camrud et al. | |
| 6,264,688 B1 | 7/2001 | Herklotz et al. | |
| 6,267,783 B1 | 7/2001 | Letendre et al. | |
| 6,270,524 B1 | 8/2001 | Kim | |
| 6,273,895 B1 | 8/2001 | Pinchuk et al. | |
| 6,273,911 B1 | 8/2001 | Cox et al. | |
| 6,273,913 B1 | 8/2001 | Wright et al. | |
| 6,287,291 B1 | 9/2001 | Bigus et al. | |
| 6,312,458 B1 * | 11/2001 | Golds | A61F 2/07 623/1.13 |
| 6,315,794 B1 | 11/2001 | Richter | |
| 6,319,277 B1 | 11/2001 | Rudnick et al. | |
| 6,322,586 B1 | 11/2001 | Monroe et al. | |
| 6,325,823 B1 | 12/2001 | Horzewski et al. | |
| 6,334,871 B1 | 1/2002 | Dor et al. | |
| 6,340,366 B2 | 1/2002 | Wijay | |
| 6,344,272 B1 | 2/2002 | Oldenburg et al. | |
| 6,348,065 B1 | 2/2002 | Brown et al. | |
| 6,350,252 B2 | 2/2002 | Ray et al. | |
| 6,350,277 B1 | 2/2002 | Kocur | |
| 6,357,104 B1 | 3/2002 | Myers | |
| 6,361,558 B1 | 3/2002 | Hieshima et al. | |
| 6,375,676 B1 | 4/2002 | Cox | |
| 6,379,365 B1 | 4/2002 | Diaz | |
| 6,383,171 B1 | 5/2002 | Gifford et al. | |
| 6,394,995 B1 | 5/2002 | Solar et al. | |
| 6,409,753 B1 | 6/2002 | Brown et al. | |
| 6,415,696 B1 | 7/2002 | Erickeson et al. | |
| 6,416,543 B1 | 7/2002 | Hilaire et al. | |
| 6,419,693 B1 | 7/2002 | Fariabi | |
| 6,425,898 B1 | 7/2002 | Wilson et al. | |
| 6,428,811 B1 | 8/2002 | West et al. | |
| 6,451,025 B1 | 9/2002 | Jervis | |
| 6,451,050 B1 | 9/2002 | Rudakov et al. | |
| 6,464,720 B2 | 10/2002 | Boatman et al. | |
| 6,468,298 B1 | 10/2002 | Pelton | |
| 6,468,299 B2 | 10/2002 | Stack et al. | |
| 6,485,510 B1 | 11/2002 | Camrud et al. | |
| 6,488,694 B1 | 12/2002 | Lau et al. | |
| 6,488,702 B1 | 12/2002 | Besselink | |
| 6,493,217 B1 | 12/2002 | Jenkins | |

(56) References Cited

U.S. PATENT DOCUMENTS

| | | |
|---|---|---|
| 6,493,220 B1 | 12/2002 | Clark et al. |
| 6,497,423 B1 | 12/2002 | Perelli et al. |
| 6,511,468 B1 | 1/2003 | Cragg et al. |
| 6,520,986 B2 | 2/2003 | Martin et al. |
| 6,520,987 B1 | 2/2003 | Plante |
| 6,527,789 B1 | 3/2003 | Lau et al. |
| 6,527,799 B2 | 3/2003 | Shanley |
| 6,529,549 B1 | 3/2003 | Norrell et al. |
| 6,530,944 B2 | 3/2003 | West et al. |
| 6,540,777 B2 | 4/2003 | Stenzel |
| 6,551,350 B1 | 4/2003 | Thornton et al. |
| 6,555,157 B1 | 4/2003 | Hossainy |
| 6,558,415 B2 | 5/2003 | Thompson |
| 6,562,067 B2 | 5/2003 | Mathis |
| 6,565,599 B1 | 5/2003 | Hong et al. |
| 6,569,180 B1 | 5/2003 | Sirhan et al. |
| 6,575,993 B1 | 6/2003 | Yock |
| 6,579,305 B1 | 6/2003 | Lashinski |
| 6,579,309 B1 | 6/2003 | Loos et al. |
| 6,582,394 B1 | 6/2003 | Reiss et al. |
| 6,582,460 B1 | 6/2003 | Cryer |
| 6,585,756 B1 | 7/2003 | Strecker |
| 6,589,273 B1 | 7/2003 | McDermott |
| 6,592,549 B2 | 7/2003 | Gerdts et al. |
| 6,599,296 B1 | 7/2003 | Gillick et al. |
| 6,599,314 B2 | 7/2003 | Mathis |
| 6,602,226 B1 | 8/2003 | Smith et al. |
| 6,602,282 B1 | 8/2003 | Yan |
| 6,605,062 B1 | 8/2003 | Hurley et al. |
| 6,605,109 B2 | 8/2003 | Fiedler |
| 6,607,553 B1 | 8/2003 | Healy et al. |
| 6,613,074 B1 | 9/2003 | Mitelberg et al. |
| 6,613,089 B1 | 9/2003 | Estes |
| 6,629,992 B2 | 10/2003 | Bigus et al. |
| 6,645,517 B2 | 11/2003 | West |
| 6,645,547 B1 | 11/2003 | Shekalim et al. |
| 6,656,212 B2 | 12/2003 | Ravenscroft et al. |
| 6,660,031 B2 | 12/2003 | Tran et al. |
| 6,660,381 B2 | 12/2003 | Halas et al. |
| 6,663,660 B2 | 12/2003 | Dusbabek et al. |
| 6,666,883 B1 | 12/2003 | Seguin et al. |
| 6,676,693 B1 | 1/2004 | Belding et al. |
| 6,676,695 B2 | 1/2004 | Solem |
| 6,679,909 B2 | 1/2004 | McIntosh et al. |
| 6,685,730 B2 | 2/2004 | West et al. |
| 6,692,465 B2 | 2/2004 | Kramer |
| 6,699,280 B2 | 3/2004 | Camrud et al. |
| 6,699,281 B2 | 3/2004 | Vallana et al. |
| 6,699,724 B1 | 3/2004 | West et al. |
| 6,702,843 B1 | 3/2004 | Brown |
| 6,709,379 B1 | 3/2004 | Brandau et al. |
| 6,709,440 B2 | 3/2004 | Matin et al. |
| 6,712,827 B2 | 3/2004 | Ellis et al. |
| 6,712,845 B2 | 3/2004 | Hossainy |
| 6,721,178 B1 | 4/2004 | Clark et al. |
| 6,723,071 B2 | 4/2004 | Gerdts et al. |
| 6,736,842 B2 | 5/2004 | Healy et al. |
| 6,743,219 B1 | 6/2004 | Dwyer et al. |
| 6,743,251 B1 | 6/2004 | Eder |
| 6,761,734 B2 | 7/2004 | Suhr |
| 6,776,771 B2 | 8/2004 | van Moorlegem et al. |
| 6,778,316 B2 | 8/2004 | Halas et al. |
| 6,790,227 B2 | 9/2004 | Burgermeister |
| 6,800,065 B2 | 10/2004 | Duane et al. |
| 6,825,203 B2 | 11/2004 | Pasternak et al. |
| 6,837,901 B2 | 1/2005 | Rabkin et al. |
| 6,840,180 B2 | 1/2005 | Ulmer |
| 6,849,084 B2 | 2/2005 | Rabkin et al. |
| 6,852,252 B2 | 2/2005 | Halas et al. |
| 6,855,125 B2 | 2/2005 | Shanley |
| 6,858,034 B1 | 2/2005 | Hijlkema et al. |
| 6,878,161 B2 | 4/2005 | Lenker |
| 6,884,257 B1 | 4/2005 | Cox |
| 6,893,417 B2 | 5/2005 | Gribbons et al. |
| 6,896,695 B2 | 5/2005 | Mueller et al. |
| 6,899,728 B1 | 5/2005 | Phillips et al. |
| 6,908,624 B2 | 6/2005 | Hossainy et al. |
| 6,913,619 B2 | 7/2005 | Brown et al. |
| 6,918,928 B2 | 7/2005 | Wolinsky et al. |
| 6,939,376 B2 | 9/2005 | Shulz et al. |
| 6,945,989 B1 | 9/2005 | Betelia et al. |
| 6,945,995 B2 | 9/2005 | Nicholas |
| 6,951,053 B2 | 10/2005 | Padilla et al. |
| 6,962,603 B1 | 11/2005 | Brown et al. |
| 6,964,676 B1 | 11/2005 | Gerberding et al. |
| 6,991,646 B2 | 1/2006 | Clerc et al. |
| 6,994,721 B2 | 2/2006 | Israel |
| 7,004,964 B2 | 2/2006 | Thompson et al. |
| 7,005,454 B2 | 2/2006 | Brocchini et al. |
| 7,022,132 B2 | 4/2006 | Kocur |
| 7,029,493 B2 | 4/2006 | Majercak et al. |
| 7,037,327 B2 | 5/2006 | Salmon et al. |
| 7,090,694 B1 | 8/2006 | Morris et al. |
| 7,101,840 B2 | 9/2006 | Brocchini et al. |
| 7,131,993 B2 | 11/2006 | Gregorich |
| 7,137,993 B2 | 11/2006 | Acosta et al. |
| 7,141,063 B2 | 11/2006 | White et al. |
| 7,147,655 B2 | 12/2006 | Chermoni |
| 7,147,656 B2 | 12/2006 | Andreas et al. |
| 7,169,172 B2 | 1/2007 | Levine et al. |
| 7,169,174 B2 | 1/2007 | Fischell et al. |
| 7,172,620 B2 | 2/2007 | Gilson |
| 7,175,654 B2 | 2/2007 | Bonsignore et al. |
| 7,182,779 B2 | 2/2007 | Acosta et al. |
| 7,192,440 B2 | 3/2007 | Andreas et al. |
| 7,208,001 B2 | 4/2007 | Coyle et al. |
| 7,208,002 B2 | 4/2007 | Shelso |
| 7,220,275 B2 | 5/2007 | Davidson et al. |
| 7,220,755 B2 | 5/2007 | Betts et al. |
| 7,223,283 B2 | 5/2007 | Chouinard |
| 7,238,197 B2 | 7/2007 | Sequin et al. |
| 7,241,308 B2 | 7/2007 | Andreas et al. |
| 7,244,336 B2 | 7/2007 | Fischer et al. |
| 7,270,668 B2 | 9/2007 | Andreas et al. |
| 7,294,146 B2 | 11/2007 | Chew et al. |
| 7,300,456 B2 | 11/2007 | Andreas et al. |
| 7,309,350 B2 | 12/2007 | Landreville et al. |
| 7,314,480 B2 | 1/2008 | Eidenschink et al. |
| 7,320,470 B1 | 1/2008 | Butera |
| 7,320,702 B2 | 1/2008 | Hammersmark et al. |
| 7,323,006 B2 | 1/2008 | Andreas et al. |
| 7,326,236 B2 | 2/2008 | Andreas et al. |
| 7,351,255 B2 | 4/2008 | Andreas |
| 7,402,168 B2 | 7/2008 | Sanderson et al. |
| 7,534,449 B2 | 5/2009 | Saltzman et al. |
| 7,699,886 B2 | 4/2010 | Sugimoto |
| 7,824,439 B2 | 11/2010 | Toyokawa |
| 7,892,273 B2 | 2/2011 | George et al. |
| 7,892,274 B2 | 2/2011 | Will et al. |
| 7,905,913 B2 | 3/2011 | Chew et al. |
| 7,918,881 B2 | 4/2011 | Andreas et al. |
| 7,922,755 B2 | 4/2011 | Acosta et al. |
| 7,938,851 B2 | 5/2011 | Olson et al. |
| 7,938,852 B2 | 5/2011 | Andreas et al. |
| 7,993,388 B2 | 8/2011 | Lee et al. |
| 8,016,870 B2 | 9/2011 | Chew et al. |
| 8,070,789 B2 | 12/2011 | Will et al. |
| 8,070,794 B2 | 12/2011 | Issenmann |
| 8,157,851 B2 | 4/2012 | Andreas |
| 8,257,427 B2 | 9/2012 | Andersen et al. |
| 8,282,680 B2 | 10/2012 | Kao et al. |
| 8,317,850 B2 | 11/2012 | Kusleika |
| 8,317,859 B2 | 11/2012 | Snow et al. |
| 8,460,358 B2 | 6/2013 | Andreas et al. |
| 8,486,132 B2 | 7/2013 | Snow et al. |
| 8,585,747 B2 | 11/2013 | Andreas et al. |
| 8,652,198 B2 | 2/2014 | Andreas et al. |
| 8,702,781 B2 | 4/2014 | Acosta et al. |
| 8,740,968 B2 | 6/2014 | Kao et al. |
| 8,956,398 B2 | 2/2015 | George et al. |
| 8,980,297 B2 | 3/2015 | Ruane et al. |
| 8,986,362 B2 | 3/2015 | Snow et al. |
| 2001/0001824 A1 | 5/2001 | Wu |
| 2001/0020154 A1 | 9/2001 | Bigus et al. |

(56) References Cited

U.S. PATENT DOCUMENTS

| | | |
|---|---|---|
| 2001/0020173 A1 | 9/2001 | Klumb et al. |
| 2001/0020181 A1 | 9/2001 | Layne |
| 2001/0035902 A1 | 11/2001 | Iddan et al. |
| 2001/0044595 A1 | 11/2001 | Reydel et al. |
| 2001/0044632 A1 | 11/2001 | Daniel et al. |
| 2001/0049547 A1 | 12/2001 | Moore |
| 2001/0049549 A1 | 12/2001 | Boylan et al. |
| 2001/0051822 A1 | 12/2001 | Stack et al. |
| 2002/0007212 A1 | 1/2002 | Brown et al. |
| 2002/0032457 A1 | 3/2002 | Sirhan et al. |
| 2002/0035395 A1 | 3/2002 | Sugimoto |
| 2002/0037358 A1 | 3/2002 | Barry et al. |
| 2002/0045914 A1 | 4/2002 | Roberts et al. |
| 2002/0052642 A1 | 5/2002 | Cox et al. |
| 2002/0087186 A1 | 7/2002 | Shelso |
| 2002/0091439 A1 | 7/2002 | Baker et al. |
| 2002/0092536 A1 | 7/2002 | LaFontaine et al. |
| 2002/0107560 A1 | 8/2002 | Richter |
| 2002/0111671 A1 | 8/2002 | Stenzel |
| 2002/0123786 A1 | 9/2002 | Gittings et al. |
| 2002/0123792 A1 | 9/2002 | Burgermeister |
| 2002/0128706 A1 | 9/2002 | Ospyka |
| 2002/0138132 A1 | 9/2002 | Brown |
| 2002/0151924 A1 | 10/2002 | Shiber |
| 2002/0151955 A1 | 10/2002 | Tran et al. |
| 2002/0156496 A1 | 10/2002 | Chermoni |
| 2002/0165599 A1 | 11/2002 | Nasralla |
| 2002/0168317 A1 | 11/2002 | Daighighian et al. |
| 2002/0177890 A1 | 11/2002 | Lenker |
| 2002/0183763 A1 | 12/2002 | Callol et al. |
| 2002/0188343 A1 | 12/2002 | Mathis |
| 2002/0188347 A1 | 12/2002 | Mathis |
| 2002/0193873 A1 | 12/2002 | Brucker et al. |
| 2003/0013266 A1 | 1/2003 | Fukuda et al. |
| 2003/0045923 A1 | 3/2003 | Bashiri et al. |
| 2003/0093143 A1 | 5/2003 | Zhao et al. |
| 2003/0097169 A1 | 5/2003 | Brucker et al. |
| 2003/0105511 A1 | 6/2003 | Welsh et al. |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 | 7/2003 | Sequin et al. |
| 2003/0125800 A1 | 7/2003 | Shulze et al. |
| 2003/0125802 A1 | 7/2003 | Callol et al. |
| 2003/0135259 A1 | 7/2003 | Simso |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0139798 A1 | 7/2003 | Brown et al. |
| 2003/0163085 A1 | 8/2003 | Tanner et al. |
| 2003/0163155 A1 | 8/2003 | Haverkost et al. |
| 2003/0176909 A1 | 9/2003 | Kusleika |
| 2003/0191516 A1 | 10/2003 | Weldon et al. |
| 2003/0195609 A1 | 10/2003 | Berenstein |
| 2003/0199821 A1 | 10/2003 | Gerdts et al. |
| 2003/0204238 A1 | 10/2003 | Tedeschi |
| 2003/0208223 A1 | 11/2003 | Kleiner |
| 2003/0212447 A1 | 11/2003 | Euteneuer |
| 2003/0225446 A1 | 12/2003 | Hartley |
| 2004/0015224 A1 | 1/2004 | Armstrong et al. |
| 2004/0024450 A1 | 2/2004 | Shulze et al. |
| 2004/0030380 A1 | 2/2004 | Shulze et al. |
| 2004/0044395 A1 | 3/2004 | Nelson |
| 2004/0047909 A1 | 3/2004 | Ragheb et al. |
| 2004/0073290 A1 | 4/2004 | Chouinard |
| 2004/0087965 A1 | 5/2004 | Levine et al. |
| 2004/0088044 A1 | 5/2004 | Brown et al. |
| 2004/0093061 A1 | 5/2004 | Acosta et al. |
| 2004/0093067 A1 | 5/2004 | Israel |
| 2004/0093077 A1 | 5/2004 | White et al. |
| 2004/0098081 A1 | 5/2004 | Landreville et al. |
| 2004/0106979 A1 | 6/2004 | Goicoechea |
| 2004/0111145 A1 | 6/2004 | Serino et al. |
| 2004/0117008 A1 | 6/2004 | Wnendt et al. |
| 2004/0138737 A1 | 7/2004 | Davidson et al. |
| 2004/0143322 A1 | 7/2004 | Litvack et al. |
| 2004/0176832 A1* | 9/2004 | Hartley .................. A61F 2/07 623/1.11 |
| 2004/0181239 A1 | 9/2004 | Dorn et al. |
| 2004/0186551 A1* | 9/2004 | Kao ....................... A61F 2/91 623/1.15 |
| 2004/0193245 A1 | 9/2004 | Deem et al. |
| 2004/0215165 A1 | 10/2004 | Coyle et al. |
| 2004/0215312 A1 | 10/2004 | Andreas et al. |
| 2004/0215319 A1 | 10/2004 | Berra et al. |
| 2004/0215331 A1* | 10/2004 | Chew .................... A61F 2/91 623/1.21 |
| 2004/0230285 A1 | 11/2004 | Gifford, III et al. |
| 2004/0230288 A1* | 11/2004 | Rosenthal ............ A61F 2/07 623/1.13 |
| 2004/0243217 A1 | 12/2004 | Andersen et al. |
| 2004/0249434 A1 | 12/2004 | Andreas et al. |
| 2004/0249435 A1 | 12/2004 | Andreas et al. |
| 2004/0249439 A1 | 12/2004 | Richter et al. |
| 2005/0004657 A1 | 1/2005 | Burgermeister |
| 2005/0010276 A1 | 1/2005 | Acosta et al. |
| 2005/0038494 A1 | 2/2005 | Eidenschink |
| 2005/0038505 A1 | 2/2005 | Shulze et al. |
| 2005/0049673 A1 | 3/2005 | Andreas et al. |
| 2005/0055077 A1 | 3/2005 | Marco et al. |
| 2005/0075716 A1 | 4/2005 | Yan |
| 2005/0080474 A1 | 4/2005 | Andreas et al. |
| 2005/0080475 A1 | 4/2005 | Andreas et al. |
| 2005/0085888 A1 | 4/2005 | Andreas et al. |
| 2005/0085897 A1 | 4/2005 | Bonsignore |
| 2005/0090846 A1 | 4/2005 | Pedersen et al. |
| 2005/0101624 A1 | 5/2005 | Betts et al. |
| 2005/0123451 A1 | 6/2005 | Nomura |
| 2005/0125051 A1 | 6/2005 | Eidenschink et al. |
| 2005/0131008 A1 | 6/2005 | Betts et al. |
| 2005/0133164 A1 | 6/2005 | Fischer et al. |
| 2005/0137622 A1 | 6/2005 | Griffin |
| 2005/0143827 A1 | 6/2005 | Globerman et al. |
| 2005/0149159 A1 | 7/2005 | Andreas et al. |
| 2005/0149168 A1 | 7/2005 | Gregorich |
| 2005/0165378 A1 | 7/2005 | Heinrich et al. |
| 2005/0171568 A1 | 8/2005 | Duffy |
| 2005/0182477 A1 | 8/2005 | White |
| 2005/0209674 A1 | 9/2005 | Kutscher et al. |
| 2005/0209676 A1 | 9/2005 | Kusleika |
| 2005/0209680 A1 | 9/2005 | Gale et al. |
| 2005/0222671 A1* | 10/2005 | Schaeffer ............ A61F 2/91 623/1.15 |
| 2005/0228477 A1 | 10/2005 | Grainger et al. |
| 2005/0245637 A1 | 11/2005 | Hossainy et al. |
| 2005/0249777 A1 | 11/2005 | Michal et al. |
| 2005/0275178 A1 | 12/2005 | Huesdash et al. |
| 2005/0278011 A1 | 12/2005 | Peckham |
| 2005/0288763 A1 | 12/2005 | Andreas et al. |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0173529 A1 | 8/2006 | Blank |
| 2006/0177476 A1 | 8/2006 | Saffran |
| 2006/0200223 A1 | 9/2006 | Andreas et al. |
| 2006/0206190 A1 | 9/2006 | Chermoni |
| 2006/0229700 A1 | 10/2006 | Acosta et al. |
| 2006/0229706 A1 | 10/2006 | Shulze et al. |
| 2006/0271150 A1 | 11/2006 | Andreas et al. |
| 2006/0271151 A1 | 11/2006 | McGarry et al. |
| 2006/0282147 A1 | 12/2006 | Andreas et al. |
| 2006/0282149 A1 | 12/2006 | Kao |
| 2006/0282150 A1 | 12/2006 | Olson et al. |
| 2006/0287726 A1 | 12/2006 | Segal et al. |
| 2007/0005127 A1* | 1/2007 | Boekstegers ........ A61F 2/2493 623/1.16 |
| 2007/0010869 A1 | 1/2007 | Sano |
| 2007/0027521 A1 | 2/2007 | Andreas et al. |
| 2007/0043419 A1 | 2/2007 | Nikolchev et al. |
| 2007/0067012 A1 | 3/2007 | George et al. |
| 2007/0088368 A1 | 4/2007 | Acosta et al. |
| 2007/0088420 A1 | 4/2007 | Andreas et al. |
| 2007/0088422 A1 | 4/2007 | Chew et al. |
| 2007/0100423 A1 | 5/2007 | Acosta et al. |

(56) References Cited

U.S. PATENT DOCUMENTS

| | | | |
|---|---|---|---|
| 2007/0100424 A1 | 5/2007 | Chew et al. |
| 2007/0106365 A1 | 5/2007 | Andreas et al. |
| 2007/0118202 A1 | 5/2007 | Chermoni |
| 2007/0118203 A1 | 5/2007 | Chermoni |
| 2007/0118204 A1 | 5/2007 | Chermoni |
| 2007/0129733 A1 | 6/2007 | Will et al. |
| 2007/0135906 A1 | 6/2007 | Badylak et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0219612 A1 | 9/2007 | Andreas et al. |
| 2007/0219613 A1 | 9/2007 | Kao et al. |
| 2007/0265637 A1 | 11/2007 | Andreas et al. |
| 2007/0270936 A1 | 11/2007 | Andreas et al. |
| 2007/0276461 A1 | 11/2007 | Andreas et al. |
| 2007/0281117 A1 | 12/2007 | Kaplan et al. |
| 2007/0292518 A1 | 12/2007 | Ludwig |
| 2008/0004690 A1 | 1/2008 | Robaina |
| 2008/0046067 A1 | 2/2008 | Toyokawa |
| 2008/0071345 A1 | 3/2008 | Hammersmark et al. |
| 2008/0077229 A1 | 3/2008 | Andreas et al. |
| 2008/0091257 A1 | 4/2008 | Andreas et al. |
| 2008/0097299 A1 | 4/2008 | Andreas et al. |
| 2008/0097574 A1 | 4/2008 | Andreas et al. |
| 2008/0125850 A1 | 5/2008 | Andreas et al. |
| 2008/0132989 A1 | 6/2008 | Snow et al. |
| 2008/0147162 A1 | 6/2008 | Andreas et al. |
| 2008/0177369 A1 | 7/2008 | Will et al. |
| 2008/0199510 A1 | 8/2008 | Ruane et al. |
| 2008/0208311 A1 | 8/2008 | Kao et al. |
| 2008/0208318 A1 | 8/2008 | Kao et al. |
| 2008/0234795 A1 | 9/2008 | Snow et al. |
| 2008/0234798 A1 | 9/2008 | Chew et al. |
| 2008/0234799 A1 | 9/2008 | Acosta et al. |
| 2008/0243225 A1 | 10/2008 | Satasiya et al. |
| 2008/0249065 A1 | 10/2008 | Webster et al. |
| 2008/0262628 A1* | 10/2008 | Laitenberger et al. ...... 623/23.7 |
| 2008/0269865 A1 | 10/2008 | Snow et al. |
| 2009/0076584 A1 | 3/2009 | Mao et al. |
| 2009/0088832 A1 | 4/2009 | Chew et al. |
| 2009/0105686 A1 | 4/2009 | Snow et al. |
| 2009/0149863 A1 | 6/2009 | Andreas et al. |
| 2009/0228088 A1 | 9/2009 | Lowe et al. |
| 2009/0234428 A1 | 9/2009 | Snow et al. |
| 2009/0248137 A1 | 10/2009 | Andersen et al. |
| 2009/0248140 A1 | 10/2009 | Gerberding |
| 2009/0264979 A1 | 10/2009 | Kao et al. |
| 2009/0276030 A1 | 11/2009 | Kusleika |
| 2010/0004729 A1 | 1/2010 | Chew et al. |
| 2011/0022148 A1 | 1/2011 | Ruane et al. |
| 2011/0093056 A1 | 4/2011 | Kaplan et al. |
| 2011/0125248 A1 | 5/2011 | George et al. |
| 2011/0152996 A1 | 6/2011 | Acosta et al. |
| 2013/0060321 A1 | 3/2013 | Kao et al. |
| 2013/0211494 A1 | 8/2013 | Snow et al. |
| 2014/0018899 A1 | 1/2014 | Snow et al. |
| 2014/0188205 A1 | 7/2014 | Andreas et al. |
| 2014/0228931 A1 | 8/2014 | Acosta et al. |
| 2014/0236282 A1 | 8/2014 | Andreas et al. |
| 2015/0142098 A1 | 5/2015 | Ruane et al. |

FOREIGN PATENT DOCUMENTS

| | | |
|---|---|---|
| DE | 1 953 1659 | 6/1997 |
| DE | 1 963 0469 | 1/1998 |
| DE | 199 50 756 | 8/2000 |
| DE | 101 03 000 | 8/2002 |
| EP | 0 203 945 B2 | 12/1986 |
| EP | 0 274 129 B1 | 7/1988 |
| EP | 0 282 143 A1 | 9/1988 |
| EP | 0 364 787 A1 | 4/1990 |
| EP | 0 505 686 | 9/1992 |
| EP | 0 533 960 | 3/1993 |
| EP | 0 596 145 | 5/1994 |
| EP | 0 696 447 A2 | 2/1996 |
| EP | 0 714 640 A1 | 6/1996 |
| EP | 0 797 963 A2 | 10/1997 |
| EP | 0 947 180 | 10/1999 |
| EP | 1 254 644 A1 | 11/2002 |
| EP | 1 258 230 | 11/2002 |
| EP | 1 266 638 B1 | 12/2002 |
| EP | 1 277 449 | 1/2003 |
| EP | 1 290 987 A2 | 3/2003 |
| EP | 1 318 765 A2 | 6/2003 |
| EP | 1 470 834 | 10/2004 |
| EP | 1 523 959 A2 | 4/2005 |
| EP | 1 523 960 A2 | 4/2005 |
| EP | 1 743 603 A2 | 1/2007 |
| GB | 2277875 A | 11/1994 |
| JP | 03-133446 | 6/1991 |
| JP | 07-132148 | 5/1995 |
| JP | 10-503663 | 4/1998 |
| JP | 10-295823 | 11/1998 |
| JP | 11-503056 T | 3/1999 |
| JP | 2935561 B2 | 8/1999 |
| JP | 2001-190687 | 7/2001 |
| JP | 2002-538932 T | 11/2002 |
| JP | 2004-121343 A | 4/2004 |
| WO | 94/27667 A1 | 12/1994 |
| WO | 95/26695 A2 | 10/1995 |
| WO | 95/29647 A2 | 11/1995 |
| WO | 96/26689 | 9/1996 |
| WO | 96/33677 | 10/1996 |
| WO | 96/37167 A1 | 11/1996 |
| WO | 96/39077 A1 | 12/1996 |
| WO | 97/10778 | 3/1997 |
| WO | 97/46174 | 12/1997 |
| WO | 97/48351 | 12/1997 |
| WO | 98/20810 | 5/1998 |
| WO | 98/37833 | 9/1998 |
| WO | 98/58600 | 12/1998 |
| WO | 99/01087 A1 | 1/1999 |
| WO | 99/47075 A1 | 9/1999 |
| WO | 99/65421 | 12/1999 |
| WO | 00/12832 A3 | 3/2000 |
| WO | 00/15151 A1 | 3/2000 |
| WO | 00/25841 | 5/2000 |
| WO | 00/32136 | 6/2000 |
| WO | 00/41649 | 7/2000 |
| WO | 00/50116 | 8/2000 |
| WO | 00/51525 A1 | 9/2000 |
| WO | 00/56237 | 9/2000 |
| WO | 00/62708 | 10/2000 |
| WO | 00/72780 | 12/2000 |
| WO | 01/26707 | 4/2001 |
| WO | 01/34063 | 5/2001 |
| WO | 01/70297 | 9/2001 |
| WO | 01/91918 A1 | 12/2001 |
| WO | 02/060344 | 8/2002 |
| WO | 02/071975 | 9/2002 |
| WO | 02/085253 A1 | 10/2002 |
| WO | 02/098326 A1 | 12/2002 |
| WO | 03/022178 A1 | 3/2003 |
| WO | 03/047651 | 6/2003 |
| WO | 03/051425 | 6/2003 |
| WO | 03/075797 | 9/2003 |
| WO | 2004/017865 | 3/2004 |
| WO | 2004/043299 A1 | 5/2004 |
| WO | 2004/043301 | 5/2004 |
| WO | 2004/043510 | 5/2004 |
| WO | 2004/052237 A2 | 6/2004 |
| WO | 2004/087006 | 10/2004 |
| WO | 2004/091441 | 10/2004 |
| WO | 2005/009295 A1 | 2/2005 |
| WO | 2005/013853 | 2/2005 |
| WO | 2005/023153 | 3/2005 |
| WO | 2006/036939 | 4/2006 |
| WO | 2006/047520 | 5/2006 |
| WO | 2007/035805 | 3/2007 |
| WO | 2007/053187 A2 | 5/2007 |
| WO | 2007/109621 | 9/2007 |
| WO | 2007/146411 | 12/2007 |

(56) References Cited

FOREIGN PATENT DOCUMENTS

| WO | 2008/005111 | 1/2008 |
|---|---|---|
| WO | 2009/0111203 | 9/2009 |

OTHER PUBLICATIONS

Colombo, "The Invatec Bifurcation Stent Solution" Bifurcation Stents: Novel Solutions, TCT 2003, Washington: Sep. 15-19, 2003, 24 pages total.
Cooley et al., "Applications of Ink-Jet Printing Technology to BioMEMs and Microfluidic Systems," Proceedings, SPIE Conference on Microfluidics and BioMEMs, (Oct. 2001).
"Drug Delivery Stent With Holes Located on Neutral Axis" Research Disclosure, Kenneth Mason Publications, Hampshire, CB, No. 429, Jan. 2000, p. 13.
Evans Analytical Group, "Functional Sites on Non-polymeric Materials: Gas Plasma Treatment and Surface Analysis," http://www.eaglabs.com.
Joung et al., "Estrogen Release from Metallic Stent Surface for the Prevention of Restenosis," J Control Release. Sep. 19, 2003;92(1-2):83-91.
Lefevre et al. "Approach to Coronary Bifurcation Stenting in 2003," Euro PCR, (May 2003) 28 pages total.
"Stent". Definitions from Dictionary.com. Unabridged 9v1.01). Retrieved Sep. 22, 2006, from Dictionary.com website: <http://dictionary.reference.com/search?q=stent>.
Stimpson et al., "Parallel Production of Oligonucleotide Arrays Using Membranes and Reagent Jet Printing," BioTechniques 25:886-890 (Nov. 1998).
Tilley, "Biolimus A9-Eluting Stent Shows Promise," Medscape Medical News, Oct. 5, 2004; retrieved from the internet: <http://www.medscape.com/viewarticle/490621>, 2 pages total.
Weir et al., "Degradation of poly-L-lactide. Part 2: increased temperature accelerated degradation," Proc Inst Mech Eng H. 2004;218(5):321-30.
Supplementary European Search Report of EP Patent Application No. 02804509, dated Dec. 13, 2006, 2 pages total.
Supplementary European Search Report of EP Patent Application No. 04749567, dated Sep. 11, 2006, 2 pages total.
Supplementary European Search Report of EP Patent Application No. 05727731.1, dated Mar. 25, 2008, 2 pages total.
Supplementary European Search Report of EP Patent Application No. 05744136, dated Mar. 26, 2008, 3 pages total.
Supplementary European Search Report of EP Patent Application No. 07758831, dated Dec. 14, 2009, 6 pages.
U.S. Appl. No. 60/336,607, filed Dec. 3, 2001, first named inventor: Bernard Andreas.
U.S. Appl. No. 60/336,767, filed Dec. 3, 2001, first named inventor: Bernard Andreas.
U.S. Appl. No. 60/336,967, filed Dec. 3, 2001, first named inventor: Sunmi Chew.
U.S. Appl. No. 60/364,389, filed Mar. 13, 2002, first named inventor: Sunmi Chew.
U.S. Appl. No. 60/440,839, filed Jan. 17, 2003, first named inventor: Bernard Andreas.
U.S. Appl. No. 60/561,041, filed Apr. 9, 2004, first named inventor: Jeffry Grainger.
U.S. Appl. No. 60/784,309, filed Mar. 20, 2006, first named inventor: Bernard Andreas.
U.S. Appl. No. 60/810,522, filed Jun. 2, 2006, first named inventor: Stephen Kaplan.
U.S. Appl. No. 60/890,703, filed Feb. 20, 2007, first named inventor: Patrick Ruane.
U.S. Appl. No. 09/097,855, filed Jun. 15, 1998, first named inventor: Enrique J. Klein; Abandoned.
U.S. Appl. No. 09/225,364, filed Jan. 4, 1999, first named inventor: Aaron V. Kaplan; Abandoned.
U.S. Appl. No. 10/874,859, filed Jun. 22, 2004, first named inventor: Pablo Acosta; Abandoned.
U.S. Appl. No. 11/462,951, filed Aug. 7, 2006, first named inventor: David Snow; Abandoned.
International Search Report and Written Opinion of PCT Application No. PCT/US2007/086864, dated May 13, 2008, 13 pages.
International Search Report and Written Opinion of PCT Application No. PCT/US2007/064319, dated Dec. 3, 2007, 15 pages.
International Search Report and Written Opinion of PCT Application No. PCT/US2008/061041, dated Nov. 7, 2008, 13 pages.
Office Action of Japanese Patent Application No. 2006-547139, dated Jun. 15, 2010, 5 pages total. (English translation included).
The State Intellectual Property Office of the Republic of China, Application No. 200880100150.2, First Office Action dated Oct. 26, 2011, 11 pages.
The State Intellectual Property Office of the People's Republic of China, Application No. 200880100150.2, Second Office Action dated Jul. 25, 2012, 23 pages.
The State Intellectual Property Office of the People's Republic of China, 200880100150.2, Third Office Action dated Apr. 12, 2013, 26 pages.
Extended European Search Report of EP Patent Application No. 08746459, dated Oct. 16, 2014, 6 pages.
Supplementary Partial European Search Report of EP Patent Application No. 05778125, dated Nov. 6, 2014, 4 pages.

\* cited by examiner

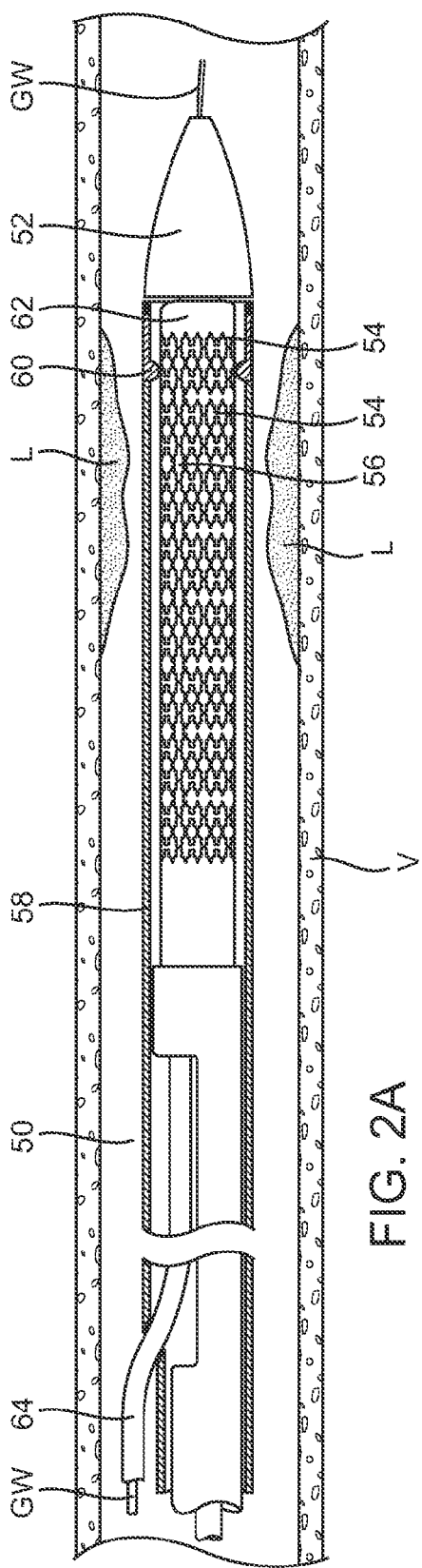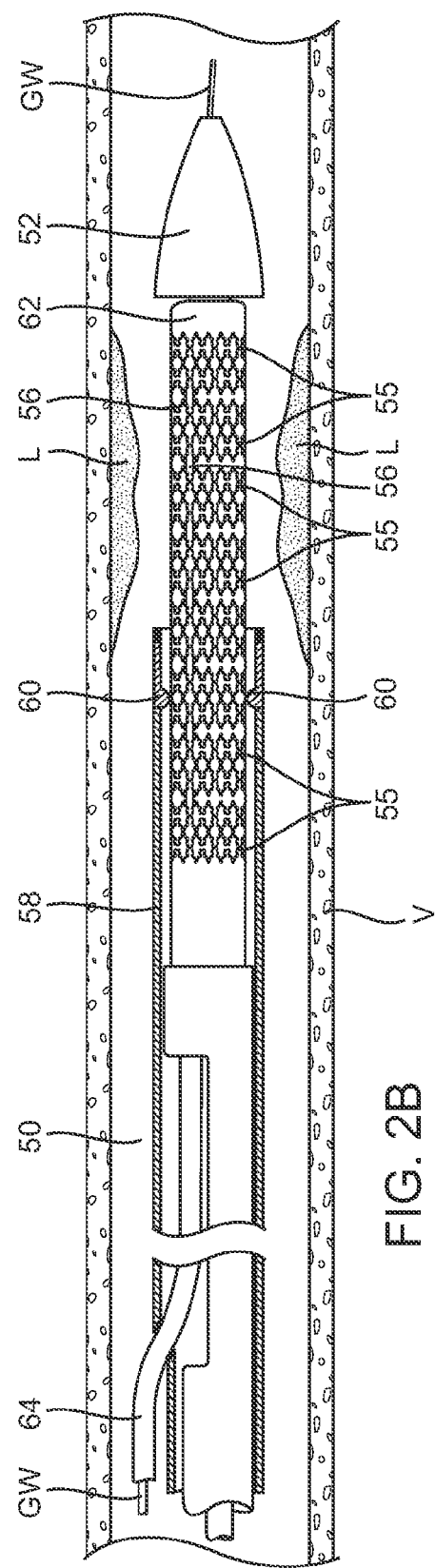

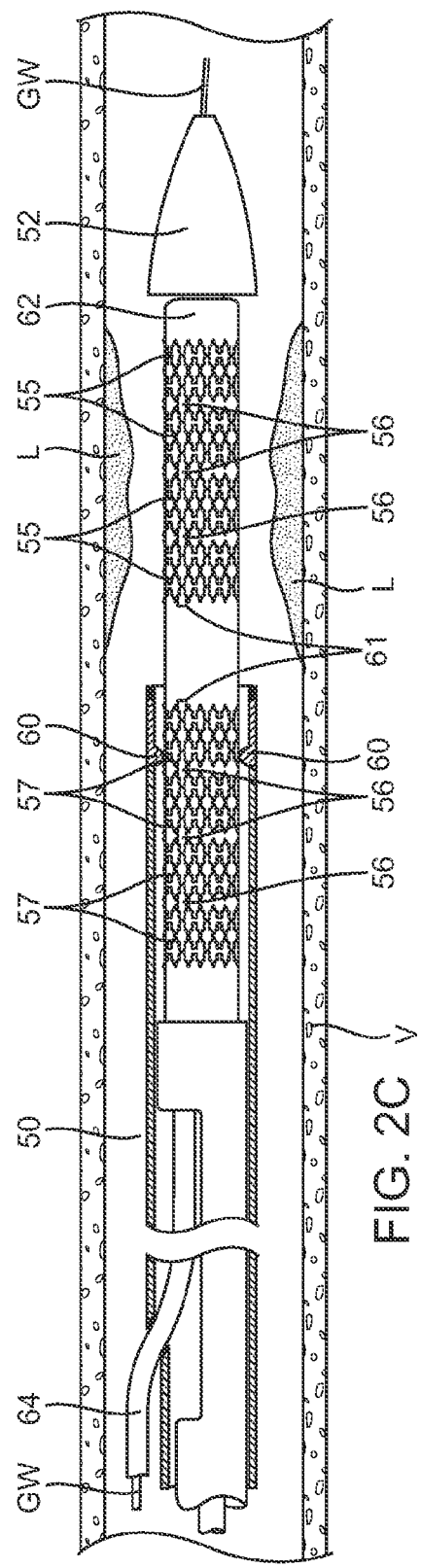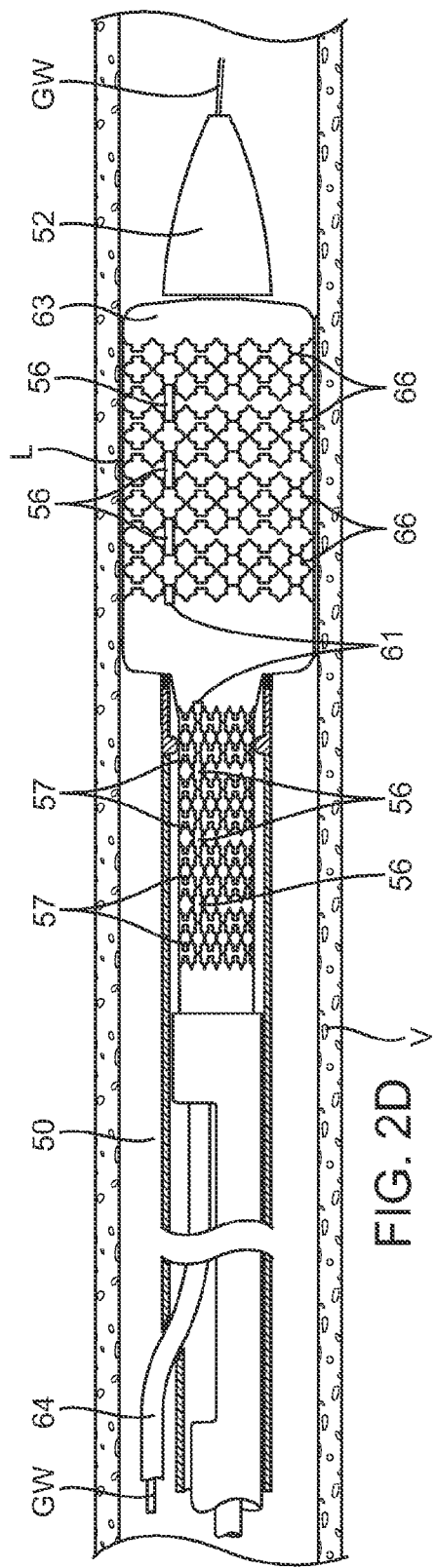

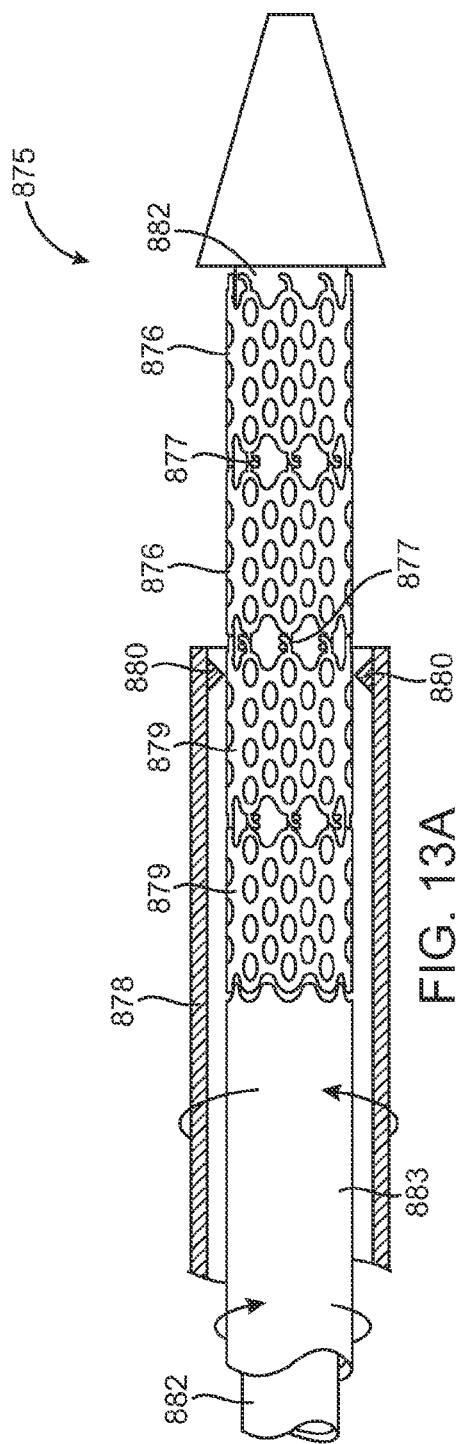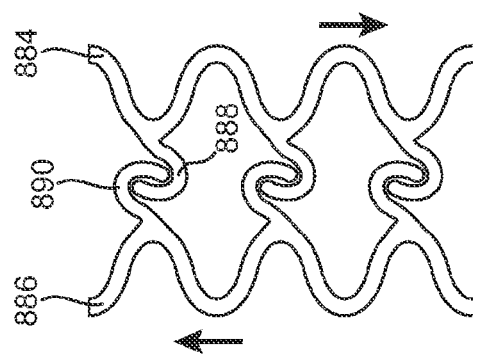
FIG. 13A
FIG. 13B

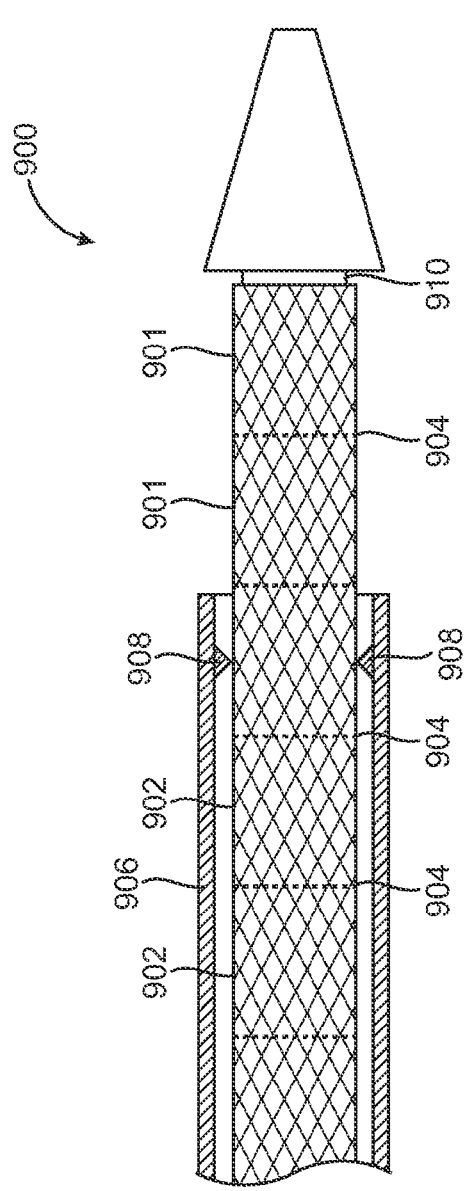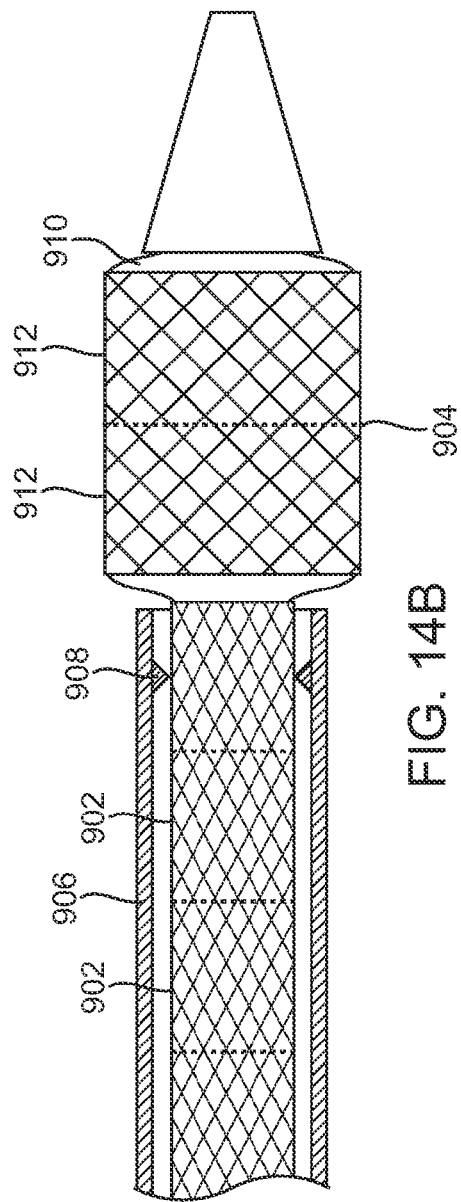

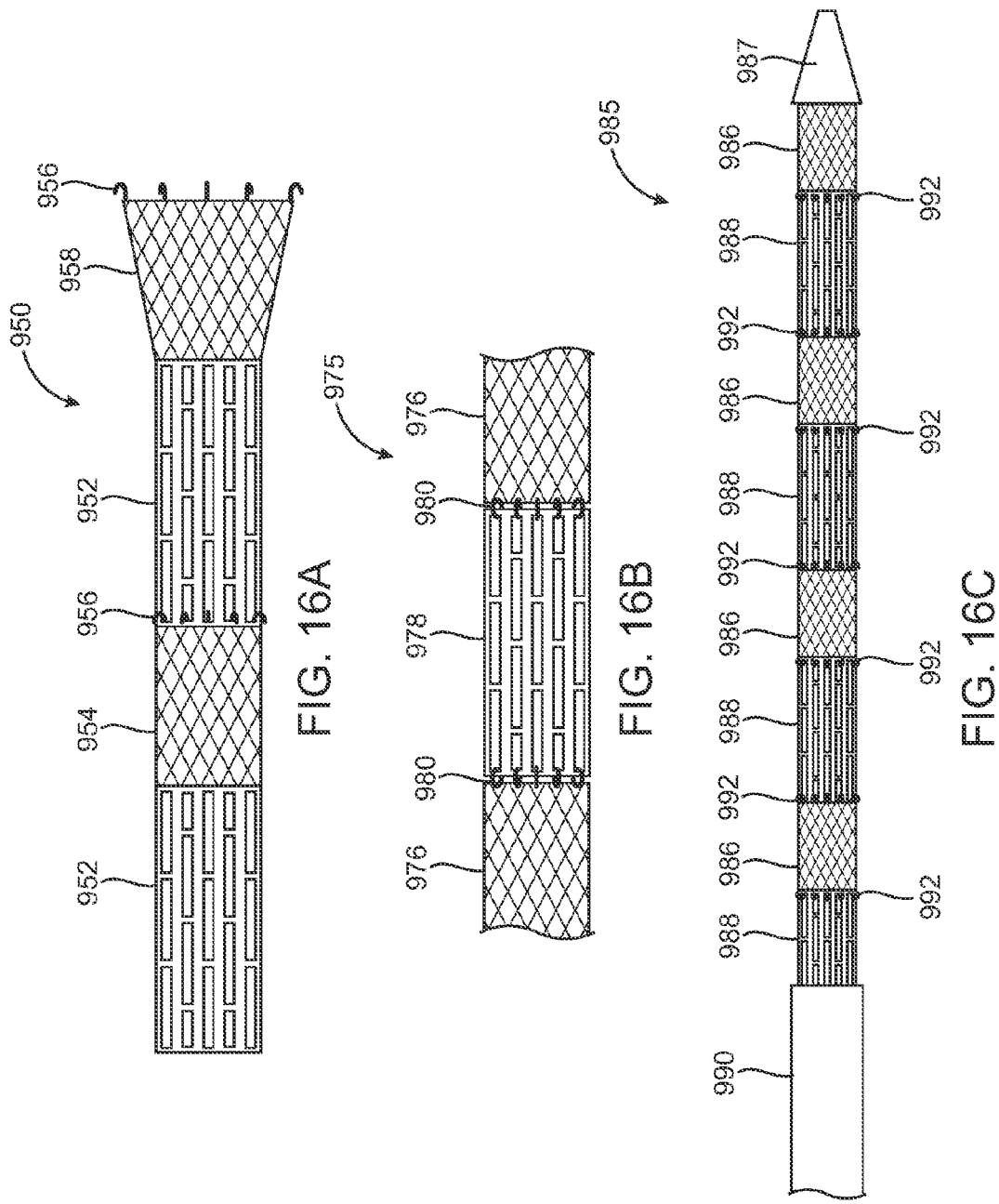

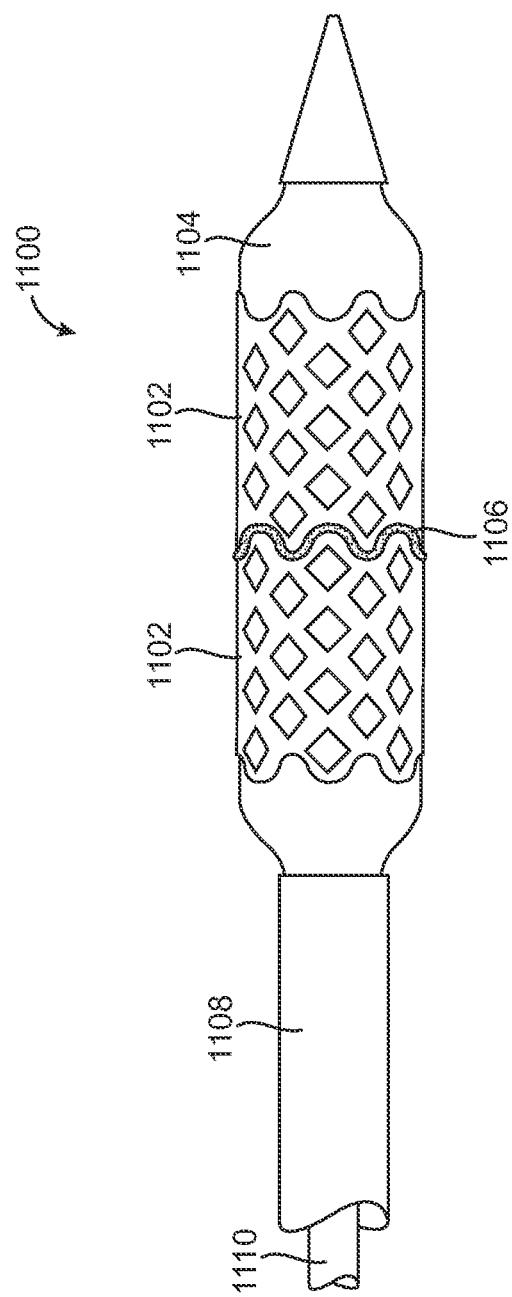

APPARATUS AND METHODS FOR DEPLOYMENT OF LINKED PROSTHETIC SEGMENTS

CROSS-REFERENCES TO RELATED APPLICATIONS

This application is a divisional of U.S. patent application Ser. No. 11/687,885 filed on Mar. 19, 2007 which is a non-provisional of U.S. Provisional Application No. 60/784,309 filed on Mar. 20, 2006, the entire contents of which are incorporated herein by reference.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention relates generally to medical devices and methods. More specifically, the present invention relates to apparatus and methods for deploying a variable length luminal medical prosthesis comprised of multiple linked or coupled prosthetic stent segments.

Stenting is an important treatment option for patients with coronary artery disease and has become a common medical procedure. The procedure is mainly directed at revascularization of stenotic vessels where a blocked artery is dilated and a stent is placed in the vessel to help maintain luminal patency. The stent is a small, tubular shaped device that can be expanded in a diseased vessel, thereby providing support to the vessel wall which in turn helps to maintain luminal patency.

Restenosis, where treated vessels such as coronary arteries tend to become re-occluded following stent implantation, was a problem in early stent technology. However, recent improvements in stent design, delivery systems and techniques along with the development of drug eluting stents have significantly reduced restenosis rates. Because of the improved efficacy of stenting, the number of stenting procedures has dramatically increased worldwide.

A balloon expandable stent, also referred to as a luminal prosthesis, is delivered to the coronary arteries using a long, flexible vascular catheter with a balloon on the distal end over which the stent is mounted. The delivery catheter is introduced into the vascular system percutaneously through a femoral, brachial, radial artery or other access point. Once the stent is delivered to the target treatment site, the delivery catheter balloon is expanded which correspondingly expands and permanently deforms the stent to a desired diameter. The balloon is then deflated and removed from the vessel, leaving the stent implanted in the vessel at the lesion site.

Self-expanding stents are another variation of luminal prosthesis where the stent is constrained during delivery and then released at a desired location. When the stent is released from the constraining mechanism, the stent resiliently expands into engagement with the vessel wall. The delivery catheter is then removed and the stent remains in its deployed position.

With current stents lesion size must be assessed in order to determine the appropriate stent length required to effectively cover the lesion. Fluoroscopy and angiography are therefore used to evaluate the lesion prior to stent delivery. A stent of appropriate size is then delivered to the lesion. Sometimes, however, lesion length cannot be assessed accurately and can result in the selection of stents which are not long enough to adequately cover the target lesion. To address this shortfall, an additional stent must be delivered adjacent to the initially placed stent. When lesion length requires multiple stents to be delivered, multiple delivery catheters are required since typically only one stent is provided with each delivery catheter. The use of multiple delivery catheters results in greater cost and longer procedure time. To overcome this shortcoming, recent stent delivery systems have been designed to streamline this process by allowing multiple stent segments to be delivered simultaneously from a single delivery catheter, thereby permitting customization of stent length in situ to match the size of lesion being treated.

Various designs have been proposed for custom length prostheses such as those described in U.S. patent application Ser. No. 10/306,813 filed Nov. 27, 2002 which is incorporated herein by reference. These designs utilize delivery systems pre-loaded with multiple stent segments, of which some or all of the stent segments can be delivered to the site of a lesion. This allows the length of the prosthesis to be customized to match the lesion size more accurately.

While the capability of customizing stent length in situ provides significant benefits over fixed length devices, it has been found that such segmented stent systems may have drawbacks under certain circumstances. For example, when vessels are highly tapered or have other irregularities in diameter, a single balloon of constant diameter may be unable to expand all of the stent segments to engage tightly with the vessel wall. In this situation, some of the segments in a multi-segment prosthesis might be under-deployed resulting in incomplete apposition with the vessel wall along the entire lesion length. This may then require a second high-pressure dilatation of the underdeployed prostheses to ensure full apposition to the vessel wall. If the segments are not fully apposed, there is a risk that they could tilt or move within the vessel.

For these and other reasons, stent delivery systems and methods are needed which can accommodate tapered vessels and minimize or prevent a stent segment from moving, dislodging or tilting in the vessel following deployment. Such stent systems should also permit stent length customization in situ and allow treatment of multiple lesions of various sizes, without requiring removal of the delivery catheter from the patient. At least some of these objectives will be met by the present invention.

BRIEF SUMMARY OF THE INVENTION

The invention provides multiple linked or coupled prosthetic stent segments along with delivery systems and methods that address the objectives outlined above and provide other advantages as well. The invention permits coupled prosthetic stent segments selected for delivery to be separated from the remaining prosthetic stent segments while an attachment between the stent segments selected for delivery is maintained or formed. This attachment results in better stent segment delivery in irregularly shaped or highly tapered vessels. Therefore, a customized, variable length, luminal medical prosthesis can be delivered effectively to one or more treatment sites in irregularly shaped or highly tapered coronary arteries or other vessels, using a single delivery device, during a single interventional procedure.

In various embodiments, stent delivery systems and methods are used to stent body lumens such as blood vessels and coronary arteries in particular. The systems and methods are also used frequently in the peripheral vascular and cerebral vascular systems as well as other body ducts such as the biliary duct, fallopian tubes and the like.

The terms "stent" and "stenting" are defined to include any of the array of expandable prostheses and scaffolds which are introduced into a lumen at a target treatment site and expanded in situ thereby exerting a radially outward force against the lumen wall. The prosthesis of the present invention comprises a closed or less preferably, an open lattice structure and are typically fabricated from a malleable or elastic material. When a malleable material is used, such as stainless steel, gold, platinum, titanium, cobalt chromium and other super alloys, the stents are typically expanded by balloon inflation, causing plastic deformation of the lattice so that it remains permanently deformed in the open position after deployment. When formed from an elastic material, including superelastic materials such as nickel-titanium alloys, the lattice structures are commonly constrained radially during delivery and upon deployment the constraining structure is removed, allowing the prosthesis to "self-expand" at the target site. The terms "stent" and "stent segments" refer broadly to all radially expansible stents, grafts, and other scaffold-like structures which are intended for deployment within a body lumen.

In a first aspect of the present invention, a method for delivering a luminal prosthesis to at least one treatment site comprises providing a plurality of radially expandable prosthetic stent segments arranged axially along a delivery catheter with at least some of the adjacent prosthetic stent segments having a coupling structure between the prosthetic stent segments. The delivery catheter is positioned at a first treatment site and two or more prosthetic stent segments are selected for deployment. The selected segments are radially expanded without expanding the segments remaining on the delivery catheter and a coupling structure permits the selected stent segments to separate from the remaining prosthetic stent segments upon differential radial expansion while an attachment is maintained or formed between the stent segments selected for deployment.

In a second aspect of the present invention a luminal prosthesis comprises a plurality of radially expandable prosthetic stent segments arranged axially. Two or more of the prosthetic stent segments are separable upon expansion from the remaining prosthetic stent segments and a coupling structure is between at least some of the adjacent prosthetic stent segments for limiting relative axial movement therebetween. The coupling structure permits a first group of the adjacent prosthetic stent segments to separate from a second group of the prosthetic stent segments upon differential radial expansion of the first group relative to the second group and the coupling structure maintains or forms an attachment between the adjacent prosthetic stent segments in the first group which have been expanded together. The coupling structure may permanently couple the adjacent prosthetic stent segments or the coupling may be biodegradable and only last long enough to permit endothelialization of the expanded prosthetic stent segments.

In another aspect of the present invention, a luminal prosthesis delivery system comprises a delivery catheter having a proximal end and a distal end along with a plurality of radially expandable prosthetic stent segments arranged axially on the distal end of the delivery catheter. A group of two or more adjacent prosthetic stent segments is separable upon expansion from the remaining prosthetic stent segments and there is a coupling structure between at least some of the adjacent prosthetic stent segments. The coupling structure permits a first group of the adjacent prosthetic stent segments to separate from a second group of prosthetic stent segments upon differential radial expansion of the first group relative to the second group. The coupling structure maintains or forms an attachment between adjacent prosthetic stent segments in the first group which have been expanded together. In some embodiments, the luminal prosthesis delivery system may further comprise a balloon disposed on the distal end of the delivery catheter.

Other embodiments of the luminal prosthesis delivery system may comprise a closing element on the distal end which, upon stent segment deployment engages the coupling structure, moving it from an open position to a closed position. The closing element may be actively controlled or passively controlled and may reflow an adhesive or polymer disposed on the prosthetic stent segments. In other embodiments, the delivery system may further comprise a decoupling element which engages the coupling element to selectively uncouple one or more coupling structures. In some other embodiments this decoupling element comprises an expandable member such as a balloon disposed on the distal end of the delivery catheter.

In various aspects of the present invention the coupling structure may comprise many different forms. For example, magnets may couple the stent segments or coupling may be achieved by overlapping the ends of adjacent prosthetic stent segments with friction or compression holding the overlapping prosthetic stent segment ends against the vessel wall. The prosthetic stent segment ends may overlap in a number of ways. In some embodiments, the stent segment ends overlap smoothly, while in others the stent segment ends interlock with one another or snap together, and still in other embodiments, the overlapping prosthetic stent segment ends couple by mating a raised surface on one prosthetic stent segment end with a corresponding depressed surface on an adjacent prosthetic stent segment end.

In other embodiments, the coupling structure can be broken by inflation of a balloon, severed with a cutting mechanism or by application of energy. Breaking or severing the coupling structure permits a first group of the prosthetic stent segments to separate from a second group of the prosthetic stent segments upon differential radial expansion of the first group relative to the second group and the coupling structure maintains an attachment between adjacent prosthetic stent segments in the first group which have been expanded together. Breaking of the coupling structure may occur while the stent segments are disposed in a sheath or after the stent segments are exposed for delivery.

The coupling structure may optionally comprise a strand of material threaded through openings in the walls of adjacent prosthetic stent segments, or a plurality of strands of material between adjacent prosthetic stent segments. The coupling structure may be threaded axially or circumferentially through the openings and may comprise a polymer or other flexible fiber or thread-like material. The coupling structure may be severed with a cutting device or by applying energy.

Many other coupling structures may be employed. For example, a coupling structure extending axially between adjacent prosthetic stent segment ends and that is movable between an open position and a closed position permits prosthetic stent segments to be coupled together when the coupling structure is moved, upon deployment, from the open position to the closed position. The coupling structure may be moved prior to expansion of the prosthetic stent segments or during their expansion. The coupling structure may be moved by an external mechanism, such as by the balloon which expands the stent segments, or by a separate mechanism on the delivery catheter.

The coupling structure may also be designed so that it is lockable under tension and releasable under compression, or rotationally lockable. Alternatively, tensioning the distal most prosthetic stent segment with a tensioner disposed on the distal end of the delivery catheter can be used to couple the distal most prosthetic stent segment to an adjacent segment.

Still, in other embodiments, the coupling structure may comprise a coating across adjacent prosthetic stent segment ends. The coating maybe a polymer, protein, sugar or other suitable material, and may be biodegradable or durable, perforated, meltable, severable, or breakable. Other embodiments include a coupling structure comprising a protuberance and a mating recess that is releasable during catheter balloon inflation. Still further, the coupling structure may comprise a deflectable portion and a coupling portion. In this embodiment, deflection of the deflectable portion releases the coupling portion from the adjacent prosthetic stent segments.

Further embodiments may have a coupling structure comprised of liquid bonding material dispensed by the delivery catheter. Alternatively, the coupling structure may comprise a self-expanding link or it may be composed of a thermal shape memory alloy or polymer that is activated to expand when exposed to a temperature change. Other coupling structures may be welded across adjacent prosthetic stent segments after their expansion or they may be bonded together.

Other aspects of the nature and advantages of the invention will become apparent from the following detailed description when taken in conjunction with the drawings.

BRIEF DESCRIPTION OF THE DRAWINGS

FIG. 2A is a side view of a luminal prosthesis delivery system with multiple linked stents mounted on a delivery catheter and positioned in a vessel, at a target lesion site.

FIG. 2B is a side view illustrating a group of stent segments selected for deployment.

FIG. 2C is a side view illustrating the stent segments selected for deployment separated from the remaining stent segments.

FIG. 2D is a side view illustrating the selected stent segments radially expanded while the remaining stent segments are left behind on the delivery catheter.

FIG. 13A shows stent segments rotationally coupled together.

FIG. 13B shows stent segment ends with hook features that may be rotationally coupled together.

FIG. 14A shows stent segments coupled together with a coating layer.

FIG. 14B shows the coupling between stent segments in FIG. 14A broken by balloon inflation.

FIG. 16A illustrates how self-expanding connecting rings may be used to couple stent segments together.

FIG. 16B shows self-expanding connecting rings linked to balloon expandable stent segments.

FIG. 16C shows a series of self-expanding connecting rings coupled to stent segments.

FIG. 18 shows stent segments welded/bonded together after deployment.

DETAILED DESCRIPTION OF THE INVENTION

Figure 1:
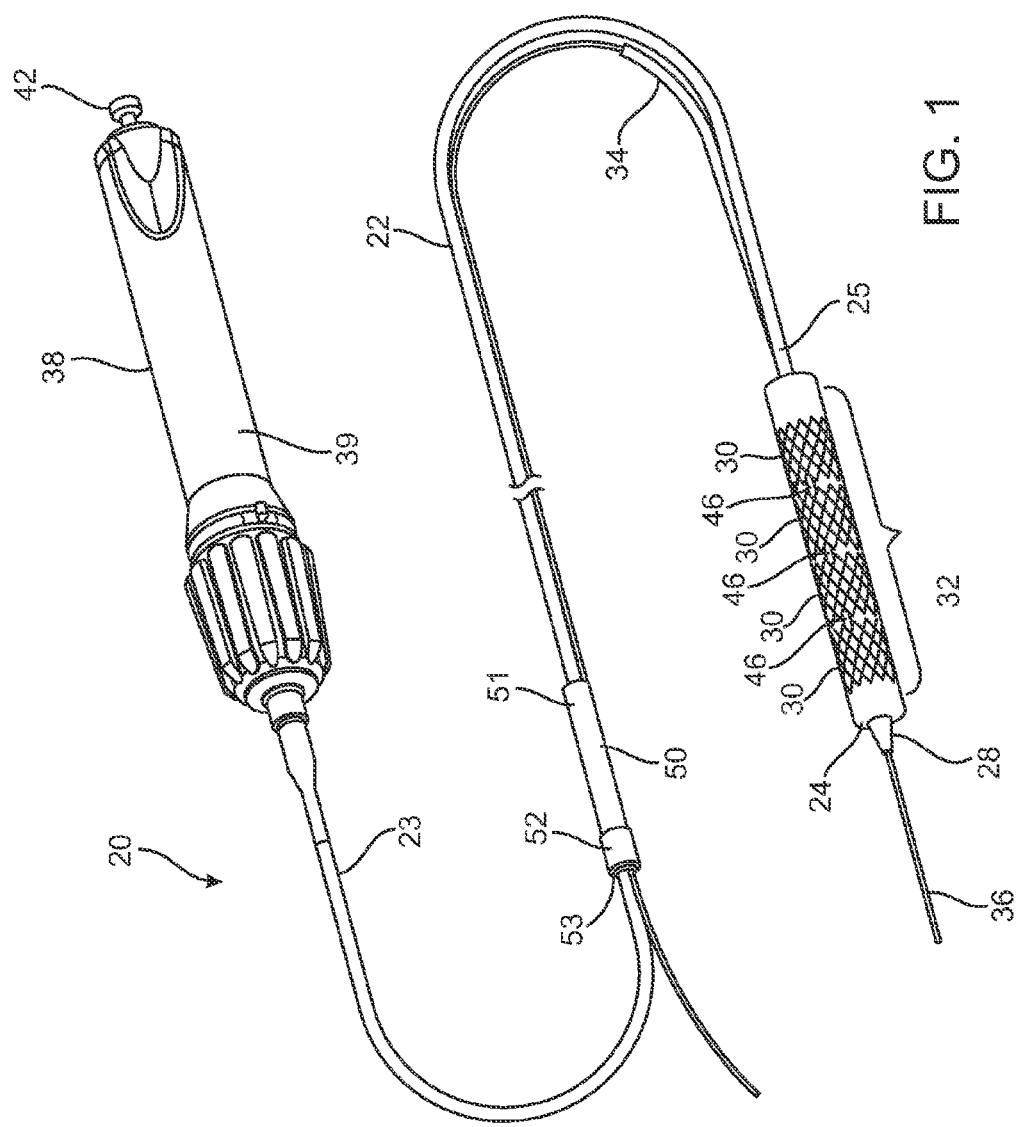
FIG. 1 shows a perspective view of a luminal prosthesis delivery system composed of multiple linked stents arranged axially along a delivery catheter.

The luminal prosthesis delivery system 20 of the present invention is illustrated in FIG. 1. Luminal prosthesis delivery system 20 comprises a catheter shaft 22 with an optional outer sheath 25 slidably disposed over an inner shaft (not shown). An inflatable balloon 24, is mounted on the inner shaft and is exposed by retracting sheath 25 relative to the inner shaft. A tapered nosecone 28, composed of a soft elastomeric material to reduce trauma to the vessel during advancement of the delivery system is attached distally of the inflatable balloon 24. A luminal prosthesis 32 comprises a plurality of separable stent segments 30 mounted over the inflatable balloon 24 for expansion. A guidewire tube 34 is slidably positioned through sheath 25 proximal to the inflatable balloon 24. A guidewire 36 is positioned slidably through guidewire tube 34, inflatable balloon 24 and nosecone 28 and extends distally thereof.

A handle 38 is attached to a proximal end 23 of the sheath 25. The handle performs several functions, including operating and controlling the catheter body 22 and the components in the catheter body. Various embodiments of the handle 38 along with details concerning its structure and operation are described in U.S. patent application Ser. No. 10/746,466, filed Dec. 23, 2003, the full disclosure of which is hereby incorporated by reference. Other handles may be employed to control delivery system 20 and are known to those skilled in the art.

In the exemplary embodiment of FIG. 1, handle 38 includes a housing 39 which encloses the internal components of the handle 38. The inner shaft is preferably fixed to the handle, while the outer sheath 25 is able to be retracted and advanced relative to handle 38. An adaptor 42 is attached to handle 38 at its proximal end and is fluidly coupled to the inner shaft in the interior of the housing of handle 38. The adaptor 42, preferably a luer connector, is configured to be fluidly coupled with an inflation device which may be any commercially available balloon inflation device such as those sold under the trade name "Indeflator™," manufactured by Abbott (formerly Guidant Corporation of Santa Clara, Calif.). The adaptor is in fluid communication with the inflatable balloon 24 via an inflation lumen in the inner shaft (not shown) to permit inflation of the inflatable balloon 24.

The outer sheath 25 and guidewire 36 each extend through a slider assembly 50 located on the catheter body 22 at a point between its proximal and distal ends. The slider assembly 50 is adapted for insertion into and sealing with a hemostasis valve, such as on an introducer sheath or guiding catheter, while still allowing relative movement of the outer sheath 25 relative to the slider assembly 50. The slider assembly 50 includes a slider tube 51, a slider body 52, and a slider cap 53.

The outer sheath 25 may be composed of any of a variety of biocompatabile materials, such as but not limited to polymers like PTFE, FEP, polyimide, or Pebax. Outer sheath 25 may also be reinforced with a metallic or polymeric braid to resist radial expansion of inflatable balloon 24. Inflatable balloon 24 may be formed of a semi-compliant polymer such as Pebax, Nylon, polyurethane, polypropylene, PTFE or other suitable polymers. Additional aspects of the luminal prosthesis delivery system are described in U.S. patent application Ser. No. 10/306,813, filed Nov. 27, 2002; U.S. patent application Ser. No. 10/637,713, filed Aug. 8, 2003; U.S. patent application Ser. No. 10/738,666, filed Dec. 16, 2003; U.S. patent application Ser. No. 11/104,305, filed Apr. 11, 2005; and U.S. application Ser. No. 11/148,585, filed Jun. 8, 2005, the full disclosures of which are hereby incorporated by reference.

The luminal prosthesis 32 is composed of one or more prosthetic stent segments 30. Prosthetic stent segments 30 are disposed over an inflation balloon 24. Each stent segment is about 2-30 mm in length, more typically about 2-20 mm in length and preferably being about 2-10 mm in length. Usually 2-50, more typically 2-25 and preferably 2-10 stent segments 30 may be positioned axially over the inflation balloon 24 and the inflation balloon 24 has a length suitable to accommodate the number of stent segments. Stent segments 30 may be positioned in direct contact with an adjacent stent segment or a space may exist in between segments. A coupling element 46 links the stent segments 30 together. Furthermore, the stent segments 30 may be deployed individually or in groups of two or more at one or multiple treatment sites within the vessel lumen.

Prosthetic stent segments 30 are preferably composed of a malleable metal so they may be plastically deformed by inflation balloon 24 as they are radially expanded to a desired diameter in the vessel at the target treatment site. The stent segments 30 may also be composed of an elastic or superelastic shape memory alloy such as Nitinol so that the stent segments 30 self-expand upon release into a vessel by refraction of the outer sheath 25. In this case, an inflation balloon 24 is not required but may still be used for predilatation of a lesion or augmenting expansion of the self-expanding stent segments (post dilation or tacking). Other materials such as biocompatible polymers may be used to fabricate prosthetic stent segments and these materials may further include bioabsorbable or bioerodable properties. Other possible biodegradable materials are disclosed below.

Stent segments 30 may have any of a variety of common constructions, such as but not limited to those described in U.S. patent application Ser. No. 10/738,666 filed Dec. 16, 2003, which was previously incorporated by reference. Constructions may include for example, closed cell constructions including expansible ovals, ellipses, box structures, expandable diamond structures, etc. In addition, the closed cells may have complex slotted geometries such as H-shaped slots, I-shaped slots, J-shaped slots, etc. Suitable open cell structures include zigzag structures, serpentine structures, and the like. Such conventional stent structures are well described in the patent and medical literature. Specific examples of suitable stent structures are described in the following U.S. patents, the full disclosures of which are incorporated herein by reference: U.S. Pat. Nos.: 6,315, 794; 5,980,552; 5,836,964; 5,527,354; 5,421,955; 4,886, 062; and 4,776,337.

In preferred embodiments, prosthetic stent segments 30 may be coated, impregnated, infused or otherwise coupled with one or more drugs that inhibit restenosis, such as Rapamycin, Everolimus, Paclitaxel, Biolimus A9, analogs, prodrugs, derivatives of the aforementioned, or other suitable agents, preferably carried in a durable or bioerodable polymeric carrier. Alternatively, stent segments 30 may be coated with other types of drugs or therapeutic materials such as antibiotics, thrombolytics, anti-thrombotics, anti-inflammatories, cytotoxic agents, anti-proliferative agents, vasodilators, gene therapy agents, radioactive agents, immunosuppressants, chemotherapeutics and/or stem cells. Such materials may be coated over all or a portion of the surface of stent segments 30, or stent segments 30 may include apertures, holes, channels, or other features in which such materials may be deposited.

FIGS. 2A-2D show how a luminal prosthesis delivery system in a vessel delivers a luminal prosthesis. In FIG. 2A, a luminal prosthesis delivery system 50 is introduced into a vessel V and advanced to the site of a lesion, L. The delivery system 50 has multiple stent segments 54 coupled together with a coupling element 56 and mounted over a delivery catheter 62. The delivery catheter has a soft nose cone 52, a guidewire tube 64 and an outer sheath 58. A stent valve element 60 disposed on the outer sheath 58 helps separate stent segments 54 selected for delivery and those remaining on the delivery catheter 62. The stent valve 60 is a polymeric or metallic material, preferably a silicone or urethane that is soft, compliant and resilient enough to provide adequate friction against a stent segment 54. Additionally, a guidewire GW passes through the guidewire tube 64 and exits the delivery catheter from the nose cone 52. In FIG. 2B, stent segments 55 are selected for deployment and exposed from the outer sheath 58 to the lesion L. In FIG. 2C the stent segments 55 selected for delivery are decoupled from the remaining stent segments 57 either by balloon inflation or by operation of the stent valve 60, as will be described in more detail below. The coupling structures 56 maintain an attachment between stent segments selected for delivery, while coupling structure(s) 61 near the distal end of sheath 58 is cut, broken, detached, or otherwise divided to separate the segments to be deployed from those to be retained in the catheter. Then in FIG. 2D a balloon 63 on the delivery catheter 62 is inflated, radially expanding stent segments 66 while the coupling structure 56 therebetween is maintained. The balloon is typically composed of a polymer such as Pebax, polyurethane or Nylon and compliance is adjusted to provide optimal inflation and stent expansion. Once expanded, the balloon 63 may be deflated and the delivery system 50 removed from the vessel or moved to the site of another lesion and the procedure repeated.

Figure 3:
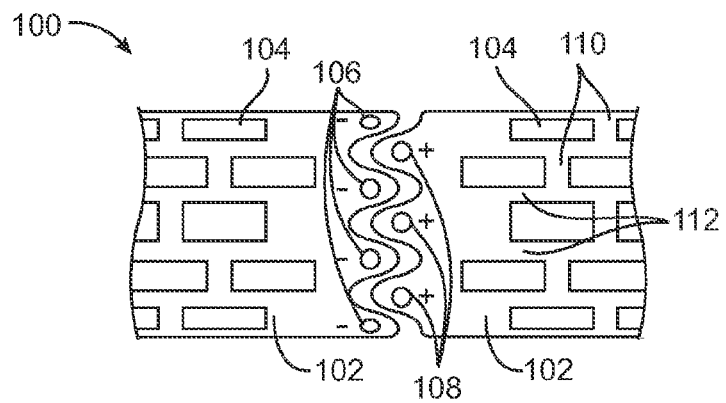
FIG. 3 shows two stent segments coupled together with magnets.

Referring now to FIG. 3, in one embodiment, a luminal prosthesis 100 is shown in a side view, and includes two or more prosthetic stent segments 102 coupled together. Each prosthetic stent segment is constructed from a series of horizontal struts 112 connected together with a series of vertical struts 110. The arrangement of horizontal struts 112 and vertical struts 110 creates rectangular shaped slots 104 which allow the stent segment 102 to expand. Other arrangements of struts are well known in the art and have previously been mentioned.

The stent segments 102 are coupled together with magnets 106 and 108 on opposite ends of adjacent stent segments. A stent segment 102 has one or more magnets 106 of a given polarity disposed on one end of the stent segment and one or more magnets 108 of the opposite polarity are disposed on the other end of stent segment 102. This allows adjacent stent segments 102 to be loaded onto a delivery catheter such that adjacent segment ends are attracted to one another, thereby coupling the segments together. Magnet strength and geometry may be selected to control the attractive forces between adjacent stent segments 102. Furthermore, FIG. 3 illustrates the ends of adjacent stent segments 102 interleaving with one another. The stent segment ends may be designed to permit different interfaces between the adjacent stent segments 102.

Figure 4A:
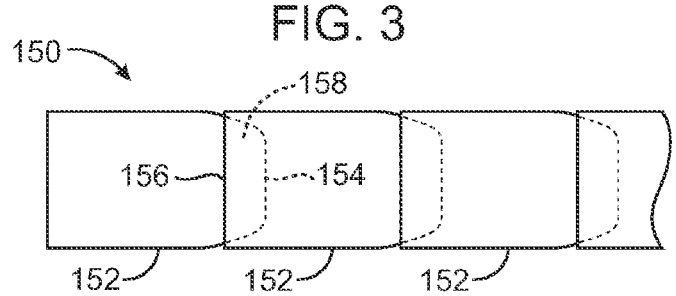
FIG. 4A shows stent segments coupled together by overlapping stent segment ends.
Figure 4B:
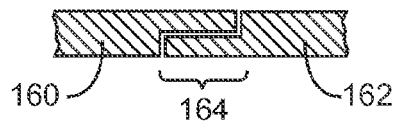
FIG. 4B illustrates stent segment ends that overlap smoothly.
Figure 4C:
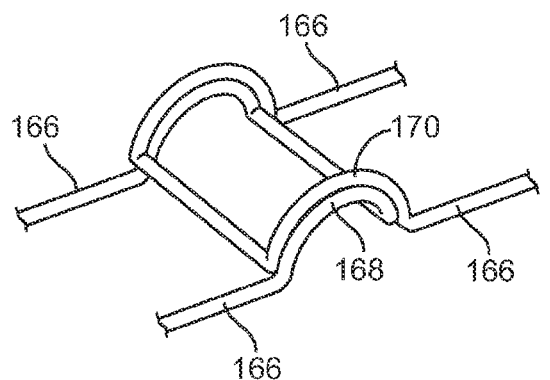
FIG. 4C illustrates stent segments coupled with overlapping arch shaped stent segment ends.
Figure 4D:
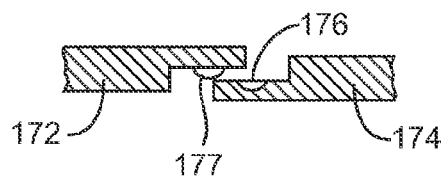
FIG. 4D shows stent segment ends that couple together by mating a raised surface with a corresponding depressed surface.

Now referring to FIG. 4A, another embodiment of the coupling structure is illustrated in a side view. In FIG. 4A, a luminal prosthesis 150 is shown comprised of multiple prosthetic stent segments 152 coupled together. In the luminal prosthesis 150, each stent segment has at least one end 154 that overlaps with an adjacent stent segment end 156, creating an overlapping region 158. Friction or compression along the overlap region 158 holds the stent segments 152 together. Several embodiments of overlapping stent segment ends are illustrated in FIGS. 4B-4D. For example, in FIG. 4B, a cross-section of the overlap region is shown. FIG. 4B shows how one stent segment end 160 overlaps smoothly over an adjacent stent segment end 162. The overlap region 164 is the same thickness as the overlapping stent segment ends 160 and 162. This provides a smooth transition between stent segment ends. FIG. 4C shows another embodiment of stent segments that overlap. In FIG. 4C, longitudinal stent struts 166 are connected by arch shaped members 168, 170 at the stent segment ends. These arch shaped members 168 and 170 overlap one another creating a coupling between adjacent stent segment ends. Other geometries on the stent segment ends, such as outwardly directed bumps or curves may be employed that allow stent segment ends to interlock or snap together. Additionally, FIG. 4D shows yet another embodiment of coupled stent segments. Building on the smooth overlapping stent segment ends previously shown in FIG. 4B, FIG. 4D shows again adjacent stent segment ends 172 and 174 that overlap smoothly. However, in FIG. 4D, the segment ends have detents 176, 177 that engage with one another, thereby enhancing engagement. Detent 177 comprises a raised surface that mates with a corresponding depressed surface in detent 176. When the detents 176 and 177 engage with one another, they overlap smoothly.

Figure 5:
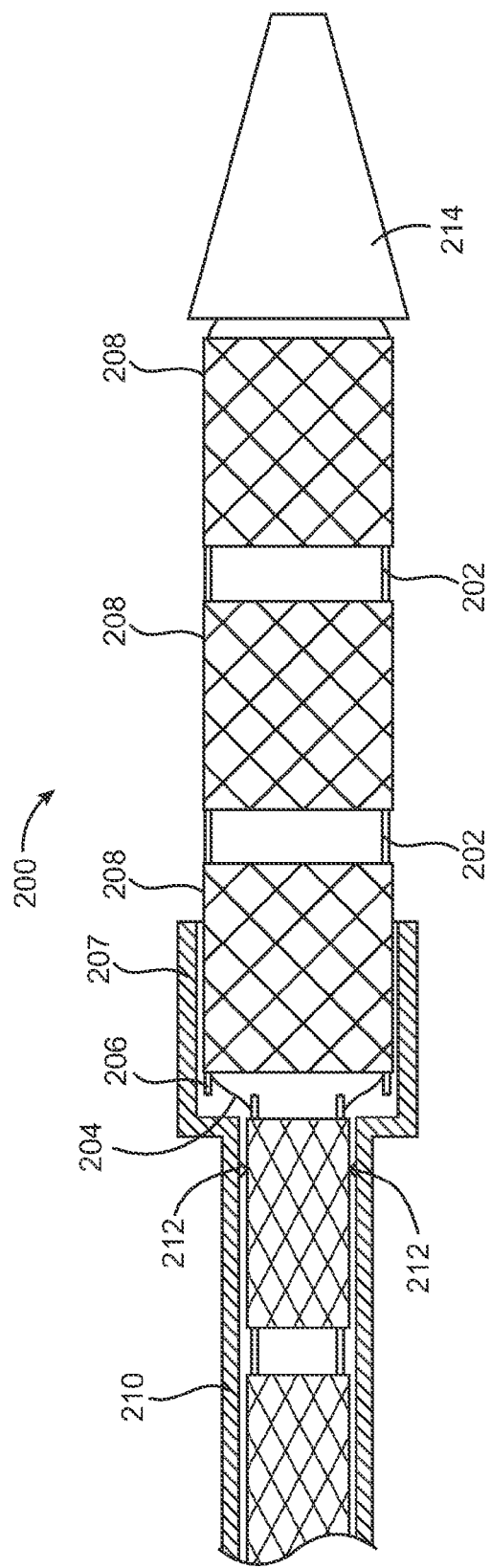
FIG. 5 shows balloon inflation breaking the coupling structure between stent segments.

In another embodiment, FIG. 5 shows a side view of a luminal prosthesis delivery system. The luminal prosthesis 200 comprises a nose cone 214, an outer sheath 210 and a plurality of stent segments 208 selected for deployment and coupled together with a breakable coupling structure 202. The selected stent segments 208 are disposed on an inflatable balloon 204. Inflation of the balloon 204 breaks the coupling 206 between the proximal most stent segment selected for delivery and the distal most stent segment remaining with the delivery system. A stent valve 212 helps retain stent segments on the delivery system that have not been selected for deployment and they are constrained by an outer sheath 210. In this embodiment, once stent segments 208 have been exposed for deployment, inflation of the balloon 204 breaks a coupling 206 between the selected and non-selected stent segments. Preferably, sheath 210 has a garage 207 at its distal end which has an enlarged inner diameter. This allows the balloon 204 to be partially inflated to break the coupling structures 206 within garage 207 by differential expansion of the stent segment within the garage relative to the immediately proximal stent segment. The two groups of segments may then be separated by a slight refraction of sheath 210, and further inflation of the balloon 204 results in full expansion of the exposed stent segments 208. Additionally, the coupling structure 202 between stent segments 208 which have been selected for deployment keep stent segments 208 coupled together during and after expansion. Coupling structures 202 may be bioerodable so as to eventually divide and at least partially erode away to decouple the implanted segments.

Figure 6A:
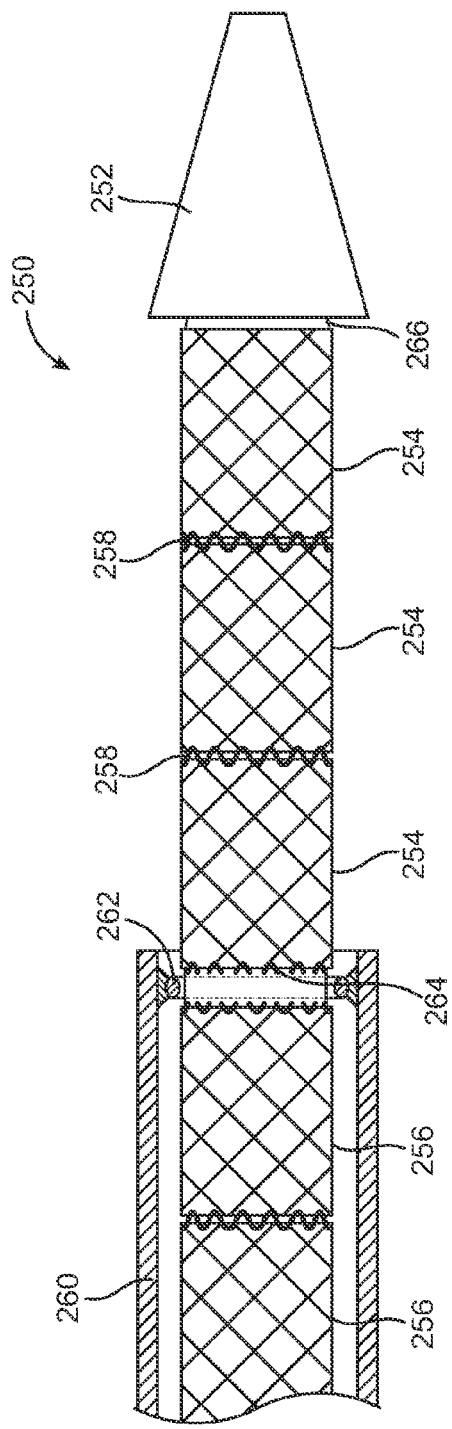
FIG. 6A shows a luminal prosthesis comprised of stent segments coupled together with a strand of material. A cutting mechanism on the delivery catheter severs the coupling structure.

With reference now to FIG. 6A, an alternative embodiment of a luminal prosthesis is illustrated. Luminal prosthesis 250 is comprised of several stent segments 254 selected for delivery and separated from the remaining stent segments 256 which remain covered by outer sheath 260. A nose cone 252 is disposed on the distal end of the delivery catheter 266 and stent segments 258 which make up the luminal prosthesis 250 are coupled together with a coupling structure 258 comprised of a single strand or a series of loops of material between adjacent stent segment ends. Coupling structure 258, comprised of a suture, fiber, or strand of durable or biodegradable polymer, is threaded around the struts on adjacent ends of pairs of prostheses 250 to link them together. The coupling structure 264 separating stent segments to be deployed and the remaining stent segments may be severed by a cutting element 262 disposed on the delivery catheter 266. The cutting element 262 may sever the coupling structure by shearing it or cutting it with sharp edges or a heating element may be employed to melt or dissolve the strand of material. Nitinol wire or other suitable metal may be used as the heating mechanism. The heating element is heated to sufficient temperature to melt and sever the coupling structure. The coupling structures 258 between stent segments 254 selected for delivery maintain an attachment during deployment. In alternative embodiments, cutting element 262 may also grab coupling structure 258 after it has been severed and retain the strand of material.

Figure 6B:
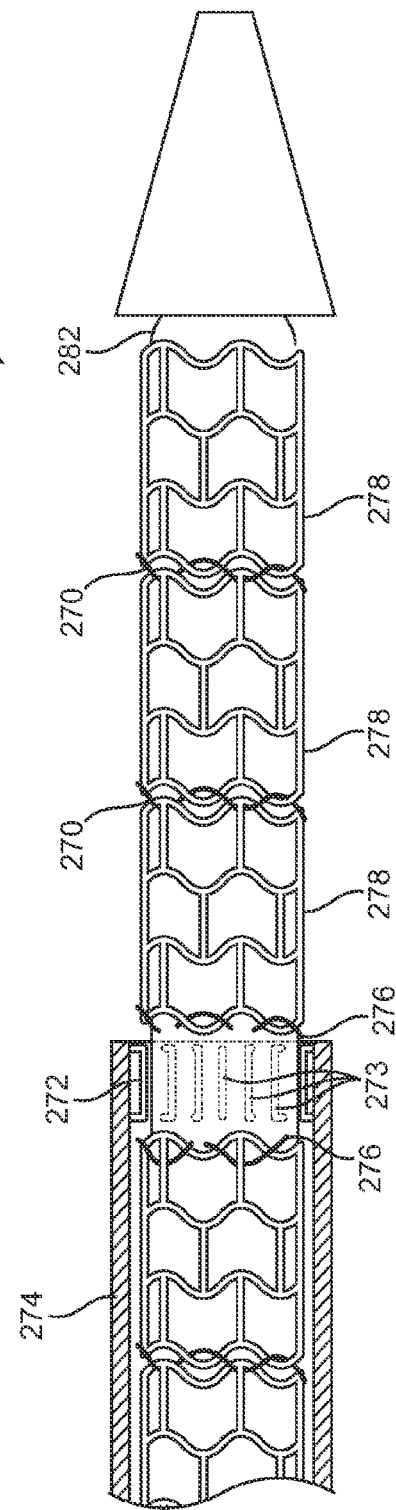
FIG. 6B shows a similar luminal prosthesis as in FIG. 6A, with an alternative cutting mechanism.

FIG. 6B shows another embodiment of a luminal prosthesis 280. Here, the prosthesis 280 is again comprised of several stent segments 278 mounted on a delivery catheter 282 and coupled together with coupling structures 270. The coupling structures 270 comprise strands of material looped circumferentially between the interleaving or nested struts of the adjacent stent segment ends. The strands may be severed by a cutting mechanism 272 disposed on the delivery catheter 282. The coupling structure 276 between stent segments 278 selected for delivery and those remaining on the delivery catheter 282, retained by an outer sheath 274, is severed with the cutting mechanism 272. The material of coupling structures 270 may be suture or strands of durable or biodegradable polymers such as polylactic acid or other flexible materials. Other possible biodegradable materials include, but are not limited to polyesters such as polyhydroxyalkanoates (PHA) and polyalphahydroxy acids (AHA). Exemplary PHAs include, but are not limited to polymers of 3-hydroxypropionate, 3-hydroxybutyrate, 3-hydroxyvalerate, 3-hydroxycaproate, 3-hydroxyheptanoate, 3-hydroxyoctanoate, 3-hydroxynonanoate, 3-hydroxydecanoate, 3-hydroxyundecanoate, 3-hydroxydodecanoate, 4-hydroxybutyrate and 5-hydroxyvalerate. Examples of AHAs include, but are not limited to various forms of polylactide or polylactic acid including PLA, PLLA or PDLLA, polyglycolic acid and polyglycolide, poly(lactic-co-glycolic acid), poly(lactide-co-glycolide), poly(ε-caprolactone) and polydioxanone. Polysaccharides including starch, glycogen, cellulose and chitin may also be used as a biodegradable material. It is also feasible that proteins such as zein, resilin, collagen, gelatin, casein, silk or wool could be used as a biodegradable implant material. Still other materials such as hydrogels including poly(hydroxyethyl methylacrylate), polyethylene glycol, poly(N-isopropylacrylamide), poly(N-vinyl-2-pyrrolidone), cellulose polyvinyl alcohol, silicone hydrogels, polyacrylamides, and polyacrylic acid are potential biodegradable implant materials. Other potential biodegradable materials include lignin, shellac, natural rubber, polyanhydrides, polyamide esters, polyvinyl esters, polyvinyl alcohol, polyalkylene esters, polyethylene oxide, polyvinylpyrrolidone, polyethylene maleic anhydride and poly(glycerol-sibacate).

The cutting mechanism may comprise multiple axially elongated cutting elements 273 arranged around the inner diameter of sheath which are flexible and can resiliently engage stent segment ends and the coupling structure therebetween. The cutting elements 273 may be sharp enough to mechanically sever the coupling strands upon partial inflation of a balloon, or may comprise heating elements that melt or burn through the strands when energized. The use of cutting elements with an axially elongated shape allows for more variability and less precision in the positioning of the stent segments 278 relative to the cutting mechanism.

Figure 6C:
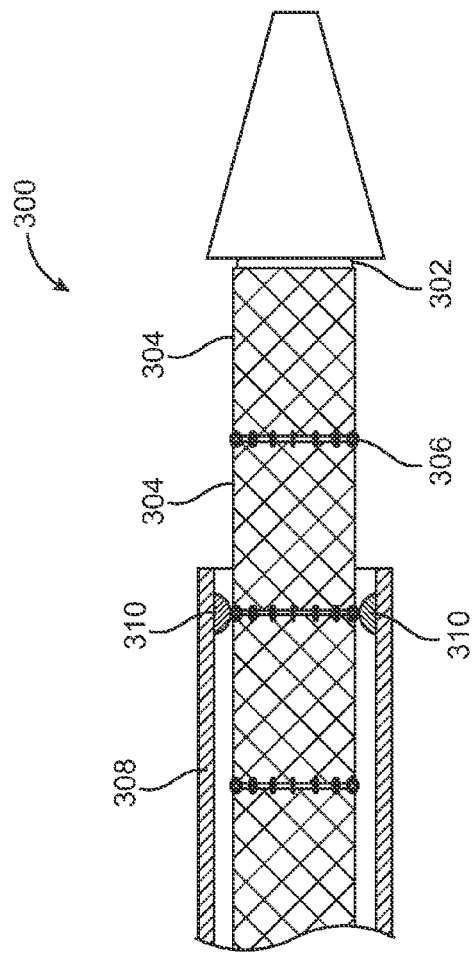
FIG. 6C shows a luminal prosthesis with a coupling structure comprised of a series of axially oriented loops of material between adjacent stent segment ends.
Figure 6E:
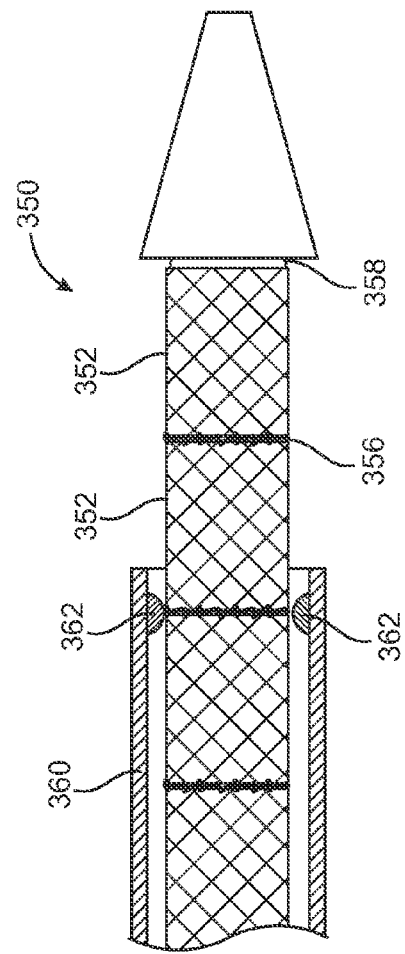
FIG. 6E shows another luminal prosthesis with a coupling structure comprised of a single strand of material circumferentially threaded through adjacent stent segment ends.
Figure 6D:
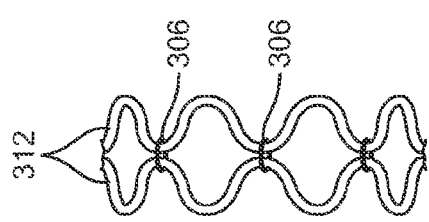
FIG. 6D shows the luminal prosthesis of FIG. 6C highlighting the coupling structure.

FIGS. 6C-D illustrate another variation on the embodiments of FIGS. 6A and 6B. FIG. 6C shows a luminal prosthesis 300 comprised of a plurality of stent segments 304 coupled together with a coupling structure 306. The stent segments 304 are disposed on a delivery catheter 302 and the coupling structure 306 is composed of a plurality of loops, bands, wires, or strands of material axially oriented between stent segment ends. The coupling structure may be fabricated from the same materials as previously described above for FIGS. 6A and 6B. Similarly, a cutting element 310 disposed on the delivery catheter 302 and preferably disposed on the outer sheath 308 can be utilized to shear, cut, melt or otherwise sever the coupling structure 306, as previously described in FIGS. 6A and 6B. FIG. 6D is a close-up view of the adjacent ends of two stent segments showing the coupling structure 306 looped around the struts of each segment. It should be understood that the adjacent stent ends 312 may also comprise nested or interleaving struts connected via coupling structures 306.

Figure 6F:
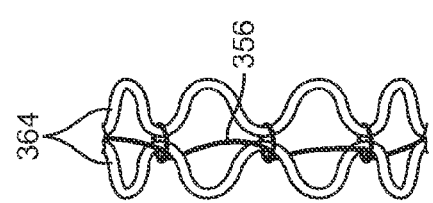
FIG. 6F shows the luminal prosthesis of FIG. 6E highlighting the coupling structure.

In yet another embodiment, FIGS. 6E-F show another variation on the coupling element between adjacent stent segments. Luminal prosthesis 350 is again comprised of several stent segments 352 with a coupling structure 356 therebetween. The stent segments 352 are mounted on a delivery catheter 358 and in this embodiment, the coupling structure comprises a single strand of material threaded circumferentially through adjacent stent segment ends. The strand in this case is continuous and is threaded in a series of loops, knots, or stitches through the struts on adjacent segment ends 364, as shown in FIG. 6F. A cutting mechanism 362 also mounted on the delivery catheter, preferably on the inner sheath 360 is used to sever the coupling structure. The materials of the coupling structure and operation of the cutting mechanism 362 may generally take the same form as previously discussed in FIGS. 6A-6D above.

Figure 7A:
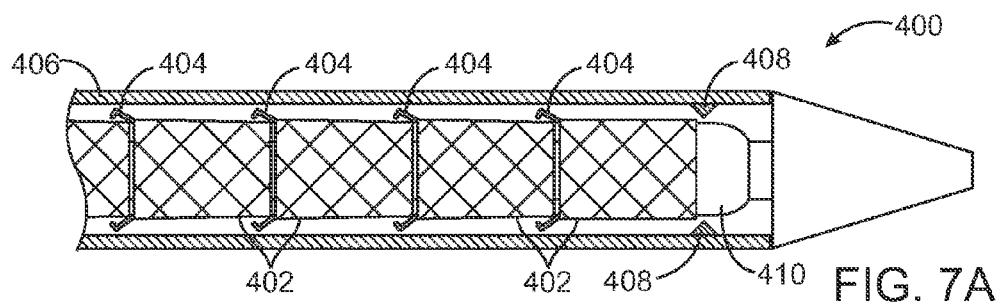
FIG. 7A shows a luminal prosthesis delivery system with a movable coupling structure.
Figure 7B:
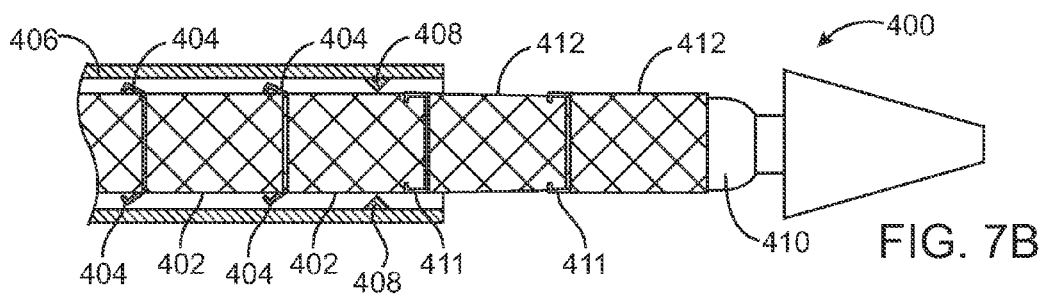
FIG. 7B shows the luminal prosthesis delivery system of FIG. 7A with some of the coupling structures closed.

FIGS. 7A and 7B illustrate another embodiment of the present invention. In FIG. 7A a luminal prosthesis delivery system 400 comprises a plurality of stent segments 402 axially arranged along an inflatable balloon 410. A series of axially oriented coupling elements 404 are disposed between adjacent stent segment ends. Initially, coupling structures 404 are angled radially outwardly, so that their free proximal ends are spaced apart from the underlying stent segment 402. The free proximal ends form a latch comprising a hooked or bent portion suitable for engaging the struts on the adjacent stent segment 402. The stent segments 402 are covered by an outer sheath 406 having a closing element 408. Prior to deployment of the stent segments 402 the coupling structures 404 remain uncoupled.

FIG. 7B illustrates how the closing element 408 closes the coupling elements 411 upon stent deployment. Stent segments 412 selected for deployment are either moved past the closing element 408 or alternatively, the closing element is moved past the selected stent segments 412 by retracting sheath 406 relative to balloon 410. As the closing element 408 engages the open coupling elements 404, the closing element 408 deflects the closing element into a closed position 411. Once closed, the coupling element 411 couples adjacent stent segments 412 together. The closing element 408 may be circumferentially offset from coupling elements 404 so that rotation of either the outer sheath 406 on which the closing element is disposed or rotation of the stent segments 402 mounted on an inflatable balloon 410, allows selective engagement between the closing element 408 and the coupling elements 404.

Figure 7C:
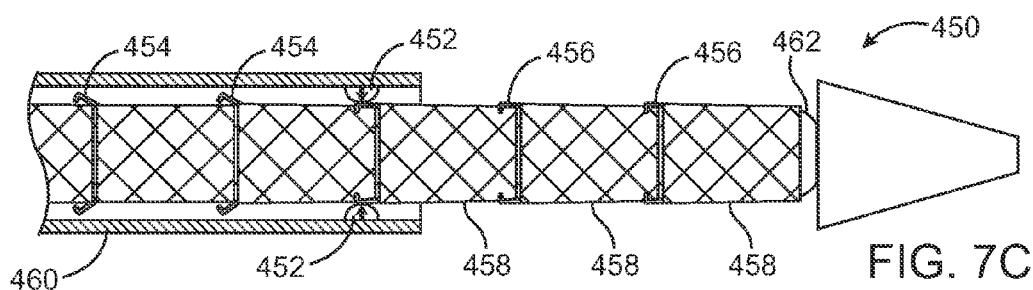
FIG. 7C shows a luminal prosthesis delivery system with an active closing element that closes the coupling structure between stent segments.

In an alternative embodiment, and with reference now to FIG. 7C, a luminal prosthesis delivery system 450 includes an inflatable balloon 462 and an active closing element 452 disposed on the outer sheath 460 which may be utilized to close coupling structures 454. In this embodiment, as stent segments 458 with open coupling elements 454 are selected for deployment and pass by closing element 452, the closing element 452 may be activated thereby engaging and closing the coupling element 456. The closing element 452 may be a balloon, which upon inflation deforms the open coupling structure to a closed configuration 456. Optionally, the closing element 452 may apply an interconnection element to the stent segments 458 as they pass through the closing element 452. For example, this may include forcing a pin from one stent segment into a mating hole in an adjacent stent segment.

Figure 7D:
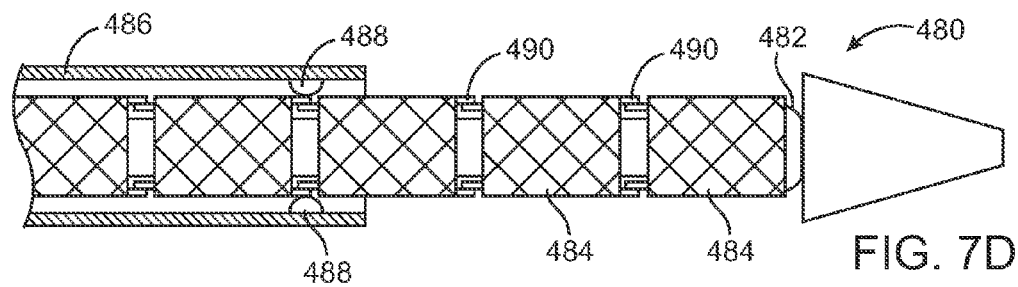
FIG. 7D shows a luminal prosthesis delivery system where an active closing element reflows an adhesive between adjacent stent segments.
Figure 7E:
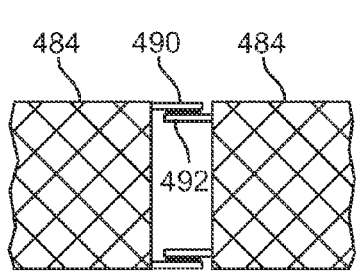
FIG. 7E shows the coupling structure formed when an active closing element reflows adhesive between adjacent stent segment ends.
Figure 7F:
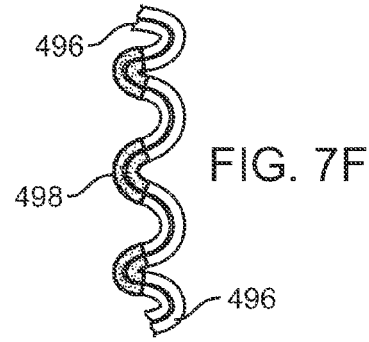
FIG. 7F further illustrates how a coupling structure may be formed when an active closing element reflows adhesive between adjacent stent segment ends.

Alternatively, in another embodiment shown in FIG. 7D, the luminal prosthesis delivery system 480 includes a plurality of stent segments 484 mounted on an inflatable balloon 482 and covered by an outer sheath 486. Coupling elements 490 attached to both ends of each stent segment overlap between adjacent stent segment ends. As the outer sheath 486 is retracted, stent segments 484 pass through a closing element 488 on the outer sheath 486. The closing element comprises a heating element that heats up an adhesive or polymer 492 on the coupling structure 490. The adhesive or polymer 492 can then reflow and when it cools down, it attaches coupling elements 490 together. FIG. 7E shows the adhesive polymer 492 between overlapping coupling elements 490 on stent segments 484. Optionally, the adhesive or polymer 498 may be reflowed across the outer surfaces of adjacent stent segment ends 496 as shown in FIG. 7F. The adhesive or polymer 498 will be selected to have sufficient strength to hold the stent segments together following expansion, sufficient resiliency and expandability to expand with the stent segments as they are deployed, appropriate melting point to be soft or liquid at a temperature which is below that which could cause vessel injury, and preferably, bioerodability so as to decompose once the stent segments are endothelialized in the vessel. One example of a suitable adhesive polymer is polylactic acid.

Figure 8A:
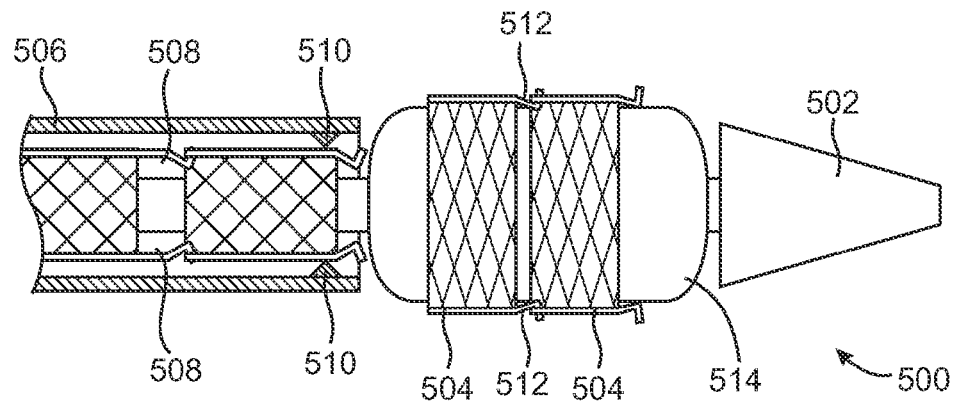
FIG. 8A shows a luminal prosthesis delivery system where the coupling elements are closed by balloon inflation.
Figure 8B:
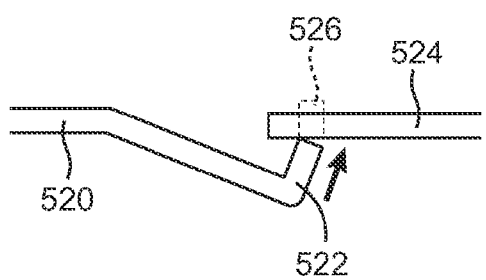
FIG. 8B shows how the coupling elements of FIG. 8A engage upon balloon inflation.
Figure 8C:
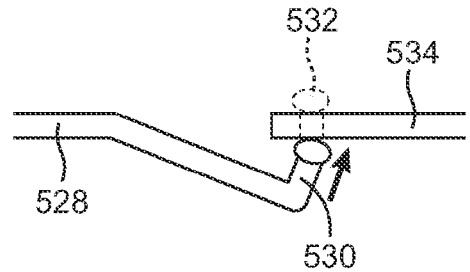
FIG. 8C illustrates another geometry where coupling elements engage during balloon inflation.

FIGS. 8A-8I illustrate embodiments in which stent segments are coupled together by expansion of a balloon or other expandable member with the stent segments. Referring to FIG. 8A, an embodiment of the luminal prosthesis delivery system 500 is illustrated with a nose cone 502 and a series of stent segments 504 mounted on the delivery system 500. Delivery system 500 includes a balloon 514 on which stent segments 504 are mounted, a sheath 506 covering stent segments 504, and a stent valve member 510 that frictionally engages stent segments 504 near the distal end of sheath 506. Linking members 512 are initially angled inwardly, disengaged from the adjacent stent segment such that stent segments 504 are decoupled from each other prior to deployment. After the desired number of stent segments 504 is exposed for deployment by retraction of sheath 506, stent valve member 510 permits the group of stent segments selected for delivery to be separated from those remaining on the delivery system. Balloon 514 then is inflated to expand the stent segments 504 selected for deployment. Radial expansion of the stent segments 504 deforms the linking member 512 therebetween, resulting in the expanded stent segments being coupled together.

Figure 8D:
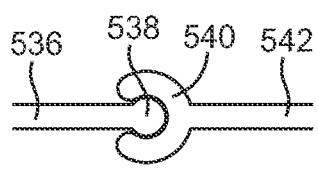
FIG. 8D shows yet another geometry where coupling elements engage during balloon inflation.
Figure 8E:
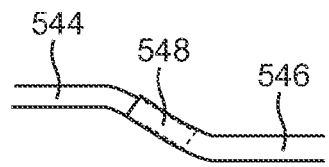
FIG. 8E is a side view of the coupling elements when they are engaged.
Figure 8F:
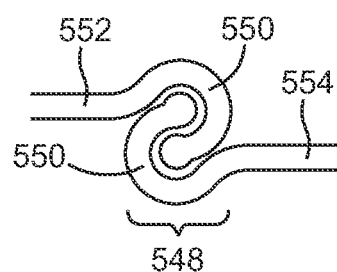
FIG. 8F is a top view of hook shaped coupling elements when engaged.
Figure 8G:
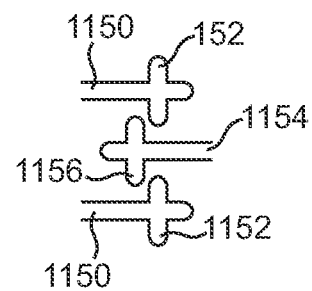
FIG. 8G shows another geometry of coupling elements adapted to engage during balloon inflation.

A number of different geometries for the coupling element 512 in FIG. 8A are possible. For example, in FIG. 8B, a pin 522 on the end of coupling element 520 mates with a corresponding hole 526 in the adjacent stent coupling element 524. Similarly, in FIG. 8C, a snap 530 on the end of one coupling element 528 has a ball tip 532 that locks into a matching hole on the adjacent coupling structure 534. FIG. 8D shows a coupling element 536 with a circular head 538 that locks into a corresponding circular recess 540 on an adjacent coupling element. When the two coupling elements 544 and 546 engage one another, they will lock together so as to have a smooth, flat transition between stent segments as shown in FIG. 8E, without protuberances into the interior or beyond the exterior surface of stent segments 504. Another geometry that allows coupling elements to interlock in a smooth, flat transition on inner and outer surfaces is shown in FIG. 8F where adjacent coupling elements 552 and 554 both have hook-like ends 550. The hooks are bent around a radial axis of stent segments 504 so as to lie generally flat on the cylindrical surface of stent segments 504. One of each pair of hooks 550 is initially angled inwardly toward balloon 514 and is deformed outwardly to be co-cylindrical with the struts of stent segment 504 as balloon 514 is expanded. The hooked ends 550 thus engage one another and lock together, coupling the expanded stent segments to one another. FIG. 8G illustrates another embodiment of an axial coupling element 1150 that couples adjacent stent segments in a similar manner to the coupling element shown in FIG. 8F. Coupling element 1150 includes a transverse strut 1152 forming a T-shape or cross that can engage and adjacent coupling element 1154 also having a transverse strut 1156. The coupling elements 1150, 1154 may be biased away from one another prior to deployment such that the transverse struts 1152, 1156 do not engage one another. Upon expansion of balloon 514, the coupling elements 1150, 1154 are deformed so that transverse struts 1152, 1156 engage, thereby coupling adjacent stent segments together. In alternative embodiments, adjacent stent segments may be engaged prior to deployment and the coupling elements 1150, 1154 may be disengaged from one another prior to or during deployment by inflating a balloon or using stent valve 510 to deflect the coupling elements 1150, 1154 away from one another.

Figure 8H:
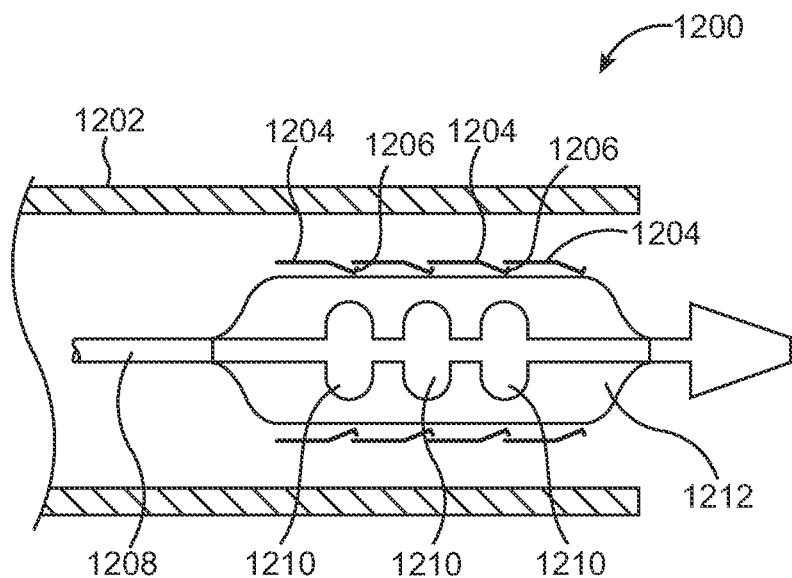
FIG. 8H illustrates a stent delivery catheter having multiple expandable members adapted to selectively interlock stent segments together.
Figure 8I:
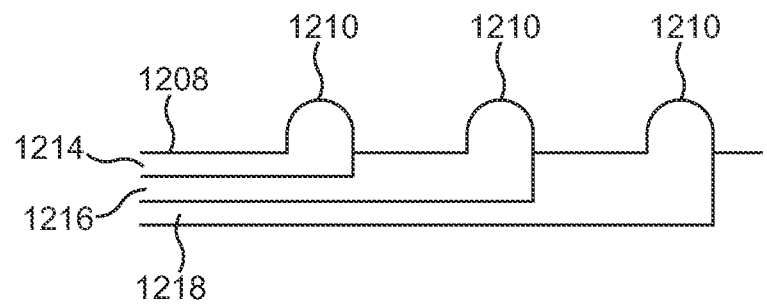
FIG. 8I illustrates multiple inflation lumens used to selectively inflate the expandable members of FIG. 8H.

FIG. 8H illustrates yet another embodiment of a stent delivery system 1200 adapted to selectively couple stent segments together. In FIG. 8H, stent delivery system 1200 includes an inner shaft 1208 with three balloons 1210 disposed thereon. The number of balloons 1210 is not meant to be limiting and more or less may be used as required. The balloons 1210 are under an outer balloon 1212 and stent segments 1204 having engageable arms 1206 are disposed over the outer balloon 1212. Multiple inflation lumens 1214, 1216 and 1218 as illustrated in FIG. 8I may be included in inner shaft 1208 to allow selective inflation of balloons 1210. Selective inflation of balloons 1210 deform engageable arms 1206 thereby interlocking adjacent stent segments 1204 together. Thus, an operator may control how many stent segments 1204 are coupled together and the stent segments 1204 may then be deployed by retracting outer sheath 1202 and expanding outer balloon 1212.

Figure 9A:
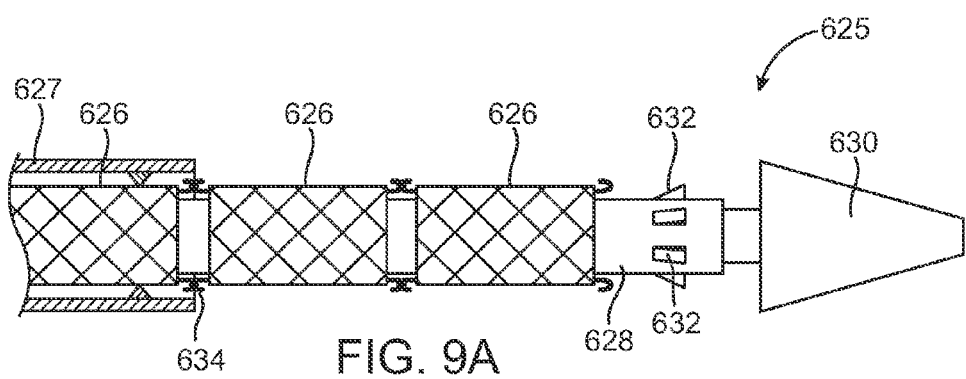
FIG. 9A shows a luminal prosthesis delivery system with releasable couplings in between stent segments.

Another embodiment of a luminal prosthesis delivery system is seen in FIG. 9A. The luminal prosthesis delivery system 625 includes a plurality of stent segments 626 mounted over a balloon 628 and covered by a sheath 627. Optionally, a stent grabber element 632 is disposed on the delivery system near the distal end of balloon 628. The stent segments 626 are connected with a coupling structure 634 which can be coupled and uncoupled. The coupling structure 634 which connects adjacent stent segment ends remains connected while under tension and may be uncoupled when adjacent stent segments 626 are pushed toward one another. Therefore, once stent segments 626 have been selected for deployment, they may be separated from the remaining stent segments by moving the outer sheath 627 distally relative to balloon 628. As stent segments 626 are being deployed the coupling structure between adjacent stent segments maintains an attachment during their expansion. The stent grabber element 632 may be utilized to engage the distal-most stent segment on balloon 628 so as to hold it in place as sheath 627 is retracted. The stent grabber element 632 may comprise a plurality of raised surfaces, bumps, hook-like elements, an annular or semi-annular ring or ridge, or an inflatable structure adapted to engage the stent segments 626.

Figure 9B:
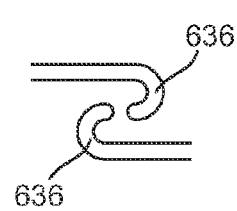
FIG. 9B shows a possible geometry of the coupling structure in FIG. 9A.
Figure 9C:
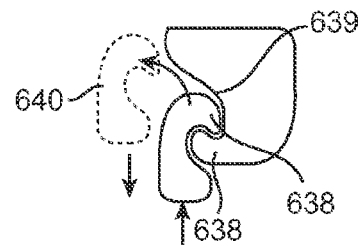
FIG. 9C shows another geometry of the coupling structure in FIG. 9A.

Various embodiments of the coupling element in FIG. 9A are proposed. For example in FIG. 9B, the coupling element may comprise hook-like ends 636 which can be releasably coupled. FIG. 9C shows another coupling element with J-shaped ends 638 that are also capable of being releasably coupled. The J-shaped ends 638 engage one another under tension. Under compression however, the curvature 639 of one coupling element acts as a cam, therefore, as the two coupling elements are pushed together, one coupling element 640 is biased away from the other coupling element, thereby decoupling the two J-shaped ends 638 from one another.

Figure 10A:
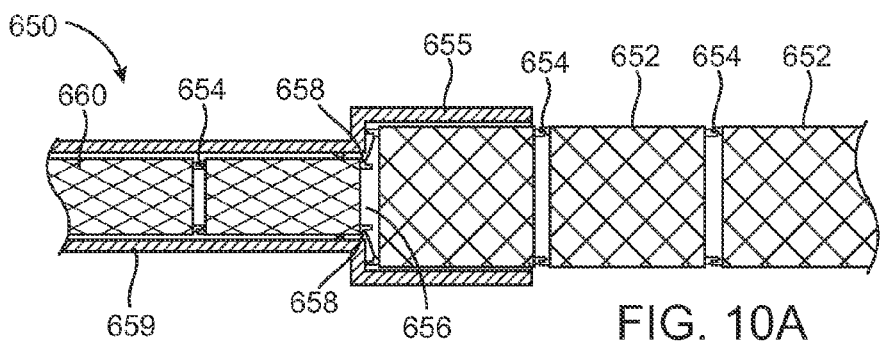
FIG. 10A shows a luminal prosthesis wherein the coupling structure between adjacent stent segments is decoupled by balloon inflation.

In another embodiment illustrated in FIG. 10A, a luminal prosthesis delivery system 650 has a plurality of stent segments 660 coupled together with a coupling structure 654. A group of stent segments 652 are selected for delivery and inflation of a balloon 656 decouples the coupling structure 658 between stent segments 652 selected for delivery from those remaining on the delivery system. The coupling structure 654 in between adjacent stent segments 652 selected for delivery maintains a connection between adjacent stent segments 652. Preferably, delivery system 650 has a garage 655 at the distal end of sheath 659 with an inner diameter slightly larger than the remainder of sheath 659. In this way, when a group of stent segments 652 has been exposed for delivery, balloon 656 may be partially inflated, thereby decoupling the coupling structures within garage 655.

Figure 10B:
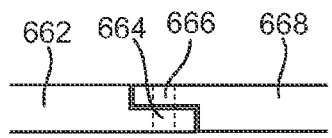
FIG. 10B shows one embodiment of the coupling structure of FIG. 10A where overlapping stent ends interlock.
Figure 10D:
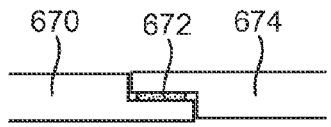
FIG. 10D shows an alternative embodiment of the coupling structure of FIG. 10A wherein an adhesive couples adjacent stent segment ends together.
Figure 10C:
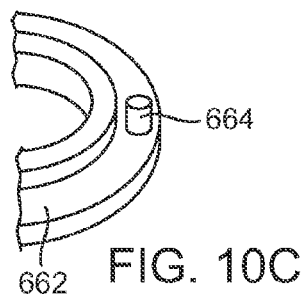
FIG. 10C shows a protuberance on one stent segment end that can form a part of the coupling structure of FIG. 10A.

The coupling element 654 may comprise a pin 664 on one end of the coupling element 662 as shown in FIGS. 10B-C, which is inserted into a mating hole 666 on the other end of the coupling element 668. Sheath 659 may then be further retracted to expose the proximal-most stent segment to be delivered, and the balloon is then fully expanded to deploy the stent segments.

Figure 10E:
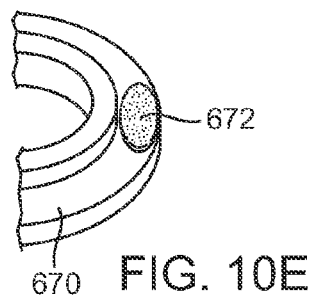
FIG. 10E shows the adhesive of FIG. 10D, applied to one stent segment end.

Alternatively, a breakable coupling element 654 may comprise an adhesive 672 shown in FIGS. 10D-E. The adhesive, which may be polylactic acid or other breakable adhesive is applied in between overlapping stent segment ends 670 and 674. Differential balloon expansion of the stent segments in garage 655 relative to those proximal thereto breaks this bond allowing stent segments to separate. Various other coupling structures are also possible, including mechanically interlocking structures as well as breakable or frangible structures.

Figure 11A:
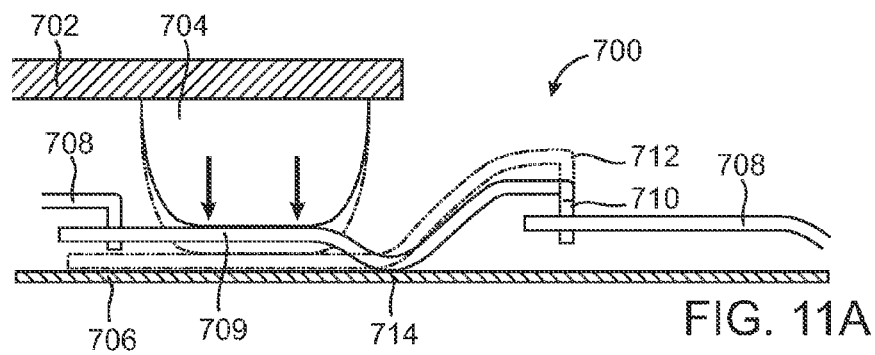
FIG. 11A shows a releasable coupling structure between adjacent stent segment ends.

With reference now to FIG. 11A, a luminal prosthesis delivery system 700 is shown with a decoupling element 704 engaging a resilient, deflectable coupling structure 709 between adjacent stent segments 708, which is mounted on an inflatable balloon 706. As stent segments 708 are exposed for deployment, they pass under the decoupling element 704 which is disposed on the outer sheath 702. The decoupling element 704 is then activated for example by inflating a balloon in the inner diameter of the outer sheath 702, or the decoupling element 704 may passively engage a coupling structure due to an interference fit. The decoupling element 704 then engages coupling element 709 and deflects it about a pivot point 714 so that a distal tip thereof moves away from the adjacent stent segment 708. Deflection of the coupling element 704 moves the coupling element from a closed position 710 to an open position 712. In the open position, the coupling element 709 is disengaged from an adjacent stent segment 708 and adjacent stent segments may be separated by moving them away from one another. Upon deactivation/deflation of the decoupling element 704, coupling structure 704 springs back to its original position.

Figure 11B:
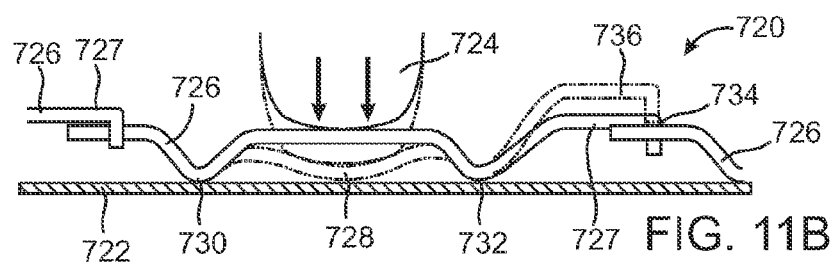
FIG. 11B shows an alternative embodiment of the releasable coupling structure of FIG. 11A.

FIG. 11B shows another embodiment in which a decoupling element 724 can be used to release a coupling element 727 between adjacent stent segments 726. In FIG. 11B, a luminal prosthesis delivery system 720 includes adjacent stent segments 726 coupled together with coupling elements 727 and mounted over an inflatable balloon 722. As the stent segments 726 are exposed for deployment they pass under the decoupling element 724 which may be similar to decoupling element 704 in FIG. 11A. The decoupling element 724 may be designed to passively engage the coupling element 727 as it passes by, or the decoupling element 724 may be actively controlled as with an inflatable balloon, for example. In either case, the decoupling element 724 engages a deflectable region of stent segment 726 and causes it to deflect about pivot points 703, 732 which in turn deflects the coupling element 727 from a closed position 734 to an open position 736. This allows a selected pair of adjacent stent segments 726 to be uncoupled from one another and the segments to be deployed may then be separated from those to remain on the delivery catheter. The coupling elements 727 are resilient so as to spring back into their original closed positions after being disengaged by decoupling element 724 so that stent segments 726 to be deployed remain coupled together following deployment.

Figure 11C:
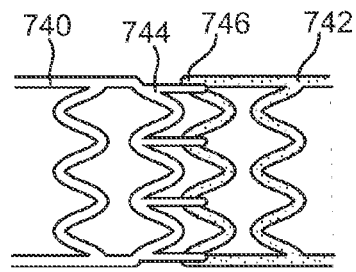
FIG. 11C illustrates overlapping stent segment ends that have the releasable coupling structure of FIG. 11A.
Figure 11D:
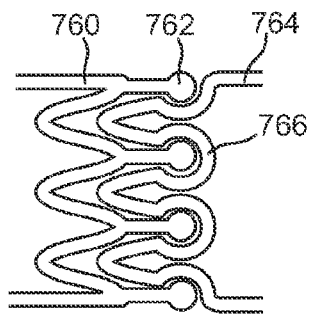
FIG. 11D shows a ball-socket coupling structure that may be employed as the coupling structure in FIG. 11A.
Figure 11E:
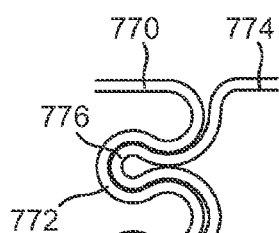
FIG. 11E shows interleaving struts that may be employed as the coupling structure in FIG. 11A.
Figure 11F:
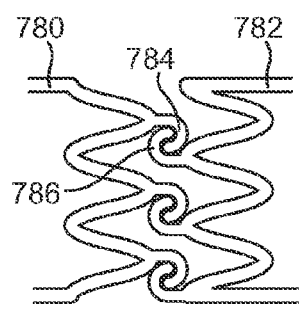
FIG. 11F shows mating hooks which may be employed as the coupling structure in FIG. 11A.
Figure 11G:
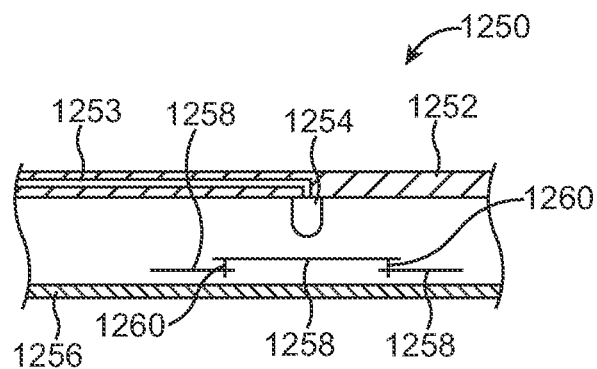
FIGS. 11G-11H show another embodiment of a releasable coupling structure.
Figure 11H:
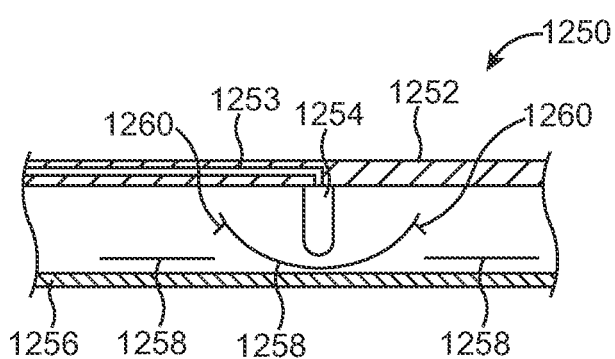

FIG. 11G shows a slight variation of the embodiments in FIGS. 11A-11B. In FIG. 11G, stent segments 1258 are disposed over balloon 1256 and the segments 1258 are coupled together with an engagement member 1260 formed from a radially inwardly facing protrusion on stent segments 1258. A decoupling element 1254 is disposed on an outer sheath 1252. The decoupling element 1254 may be expanded as seen in FIG. 11H so as to engage and compress stent 1258, thereby compressing it and causing the ends of stent 1258 to flare outwardly disengaging adjacent stent segments 1258. A lumen 1253 in sheath 1252 may be used to inflate and deflate the decoupling element 1254.

FIG. 11C shows how adjacent stent segments 740, 742 can be coupled together with the coupling mechanism described in FIGS. 11A and 11B. Here, a stent segment 740 has a coupling element 744 extending axially and disposed over an adjacent stent segment 742. The adjacent stent segment 742 has an end 746 adapted to engage with the axial coupling element 744.

Several geometries of the coupling element described in FIGS. 11A and 11B are possible. For example, FIGS. 11D through 11F show how coupling elements between adjacent stent segments may engage one another. FIG. 11D shows circular ends 762 on one stent segment end 760 mating with a corresponding circular end 766 on the adjacent stent segment end 764 forming a ball and socket, while in FIG. 11E a serpentine pattern 772 on one stent segment end 770 interlocks with a matching serpentine pattern 776 on the adjacent stent segment end 774, forming interleaving ends. Hook-like stent segment ends 784, 786 on adjacent stent segment ends 780, 782 are also shown in FIG. 11F.

Figure 12A:
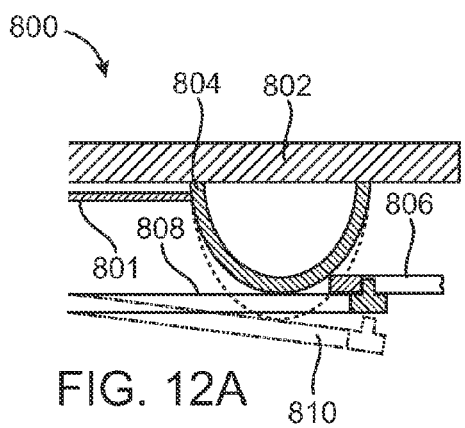
FIG. 12A illustrates an inflatable decoupling element.
Figure 12B:
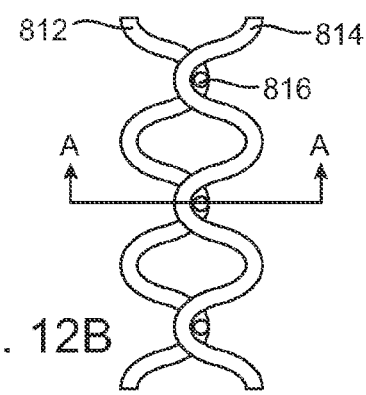
FIG. 12B shows overlapping stent segment ends releasably coupled.
Figure 12C:
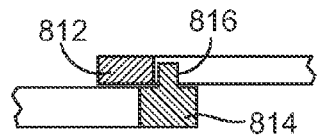
FIG. 12C is a cross-sectional view of overlapping stent segment ends in FIG. 12B.

Other embodiments of coupling mechanism in FIGS. 11A and 11B are still possible. For example, in FIGS. 12A-C, a decoupling element 804 is shown in a drawing illustrating the distal end of a luminal prosthesis delivery system 800. Here, a decoupling element 804 is again mounted on an outer sheath 802. The decoupling element, which may be either active or passive, works similarly as previously described and is capable of uncoupling coupling elements 810 between adjacent stent segments. The decoupling element 804 deflects one end of the stent segment 808 inwardly, moving coupling element 810 into an uncoupled position. Coupling element 810 may comprise a pin or protuberance 816 which extends from one stent segment end 814 and engages an adjacent stent segment end 816 which overlaps stent segment end 814. In some embodiments the decoupling element 804 may be an inflatable balloon with an inflation lumen 801 in or alongside sheath 802.

Figure 12D:
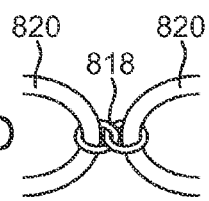
FIG. 12D illustrates breakable chain linked coupling elements between stent segments.
Figure 12E:
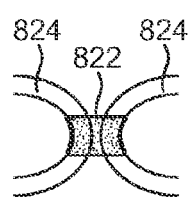
FIG. 12E illustrates an adhesive coupling element between stent segments.
Figure 12F:
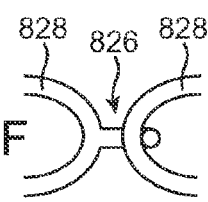
FIG. 12F shows a hook/ring coupling element between stent segments.
Figure 12G:
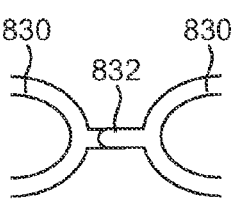
FIG. 12G shows mating hooks coupling stent segments together.
Figure 12H:
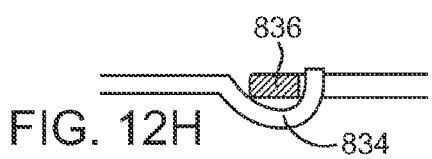
FIGS. 12H-12L show various geometries of interlocking stent segment ends.
Figure 12K:
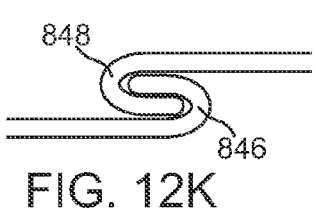
Figure 12I:
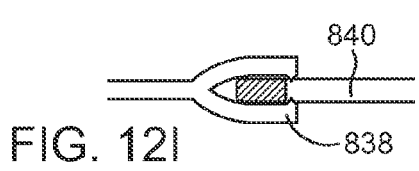
Figure 12L:
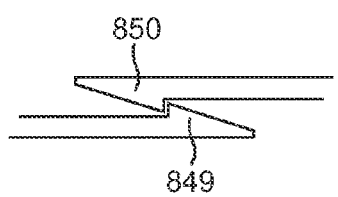
Figure 12J:
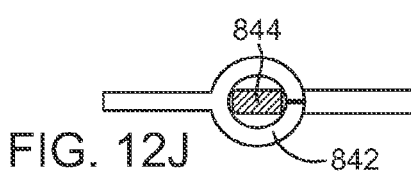

Alternative couplings are shown in FIGS. 12D through 12L. FIG. 12D shows breakable chain links 818 between adjacent stent segment ends 820, while FIG. 12E shows a breakable glue or polymer 822 between adjacent stent segment ends 824. FIGS. 12F and 12H illustrate a hook/ring coupling 826 between adjacent stent segment ends 828 with offset hooks 834, 836. FIGS. 12G, K, and L depict mating hooks 832 between the adjacent stent segment ends 830. J-shaped hooks 846, 848 engage one another in FIG. 12K and ramped flanges or catches 849 and 850 engage in FIG. 12L. In FIG. 12I a pair of jaws 838 engage a strut 840 on the adjacent stent segment. Circular shaped jaws 842 are shown in FIG. 12J engaging a strut 844 on the adjacent stent segment. The above-mentioned hooks or jaws may be composed of a resilient or deformable material that can be deflected to open the jaws or deflect the hooks when sufficient radial or axial force is applied to the stent segment to which the jaws or hooks are attached. For example, if a balloon is used to expand a selected group of stent segments, the differential expansion of adjacent stent segments will decouple the links, hooks, jaws, or catches between the stent segments.

Now referring to FIG. 13A, a luminal prosthesis delivery system 875 is shown with rotationally disengageable couplings 877. Here, a plurality of stent segments 876, 879 are disposed on a delivery catheter 882 and coupled together with L-shaped couplings 877 that can be disengaged. A stent valve 880 disposed on the outer sheath 878, comprising an annular flange or ring of slightly reduced diameter, a series of bumps or protrusions, or other suitable structure engages stent segment 876. Stent valve 880 may be a passive structure operating through friction against stent segments 876, or an active member such as an inflatable balloon. This way, the catheter shaft 882 can be rotated which turns stent segments selected for delivery 876 relative to the remaining stent segments 879, thereby releasing the coupling 877 between the two groups, allowing stent segments 876 to be delivered. A pusher element 883 disposed on the catheter shaft 882 may also be used to help rotate the stent segments into the disengaged position. FIG. 13B illustrates more clearly the coupling structure between adjacent stent segments. Here, adjacent stent segments 884, 886 each have hook shaped or L-shaped coupling structures 888, 890 which are engaged and may be rotationally disengaged. Alternatively, the outer sheath 878 may be adapted to twist automatically as it is retracted, thereby decoupling stent segments within the outer sheath from those exposed outside of it.

A coating layer may also be utilized as the coupling structure between adjacent stent segments, as illustrated in FIG. 14A. A luminal prosthesis delivery system 900 is shown in FIG. 14A including stent segments 901, 902 disposed on a delivery catheter balloon 910. To expose stent segments 901 for deployment, the outer sheath 906 is pulled back relative to balloon 910. A coating layer of a breakable or otherwise severable material is disposed over adjacent stent segments 901, 902 which couples and/or encapsulates the stent segments together. A perforation 904 may be used in between adjacent stent segments to assist in their separation during delivery. Turning now to FIG. 14B, stent segments 912 which were selected for delivery are now radially expanded by inflation of balloon 910. The coating layer maintains an attachment between the expanded stent segments 912 while the coating layer between expanded stent segments 912 and stent segments 902 remaining on the delivery catheter has been broken by the differential expansion thereof. The coating layer also maintains an attachment between adjacent stent segments 902 not selected for delivery. One exemplary material that may be used as such a coating layer is polylactic acid, however a variety of breakable, cuttable, or meltable polymers and other materials may be employed. A heating or cutting element located near the distal end of sheath 906 and similar to cutting element 272 in FIG. 6B may optionally be used to sever the coating between adjacent stent segments.

The coating material may comprise any of a variety of durable and bioerodible materials including polymers, ceramics, proteins, sugars and others. Other coating materials may include poly(styrene-b-isobutylene-b-styrene) or SIBS, polyethylene-co-vinyl acetate (PEVA) and poly n-butyl methacrylate (PBMA). Preferably, the coating layer is the same as that used as a coating on the stent segments for carrying therapeutic agents, such as anti-restenosis drugs, thrombolytics, and the like. In such embodiments, the coating layer may extend over substantially all of the outer surface of each stent segment, with portions of the coating bridging between adjacent segments to create couplings therebetween.

Figure 15A:
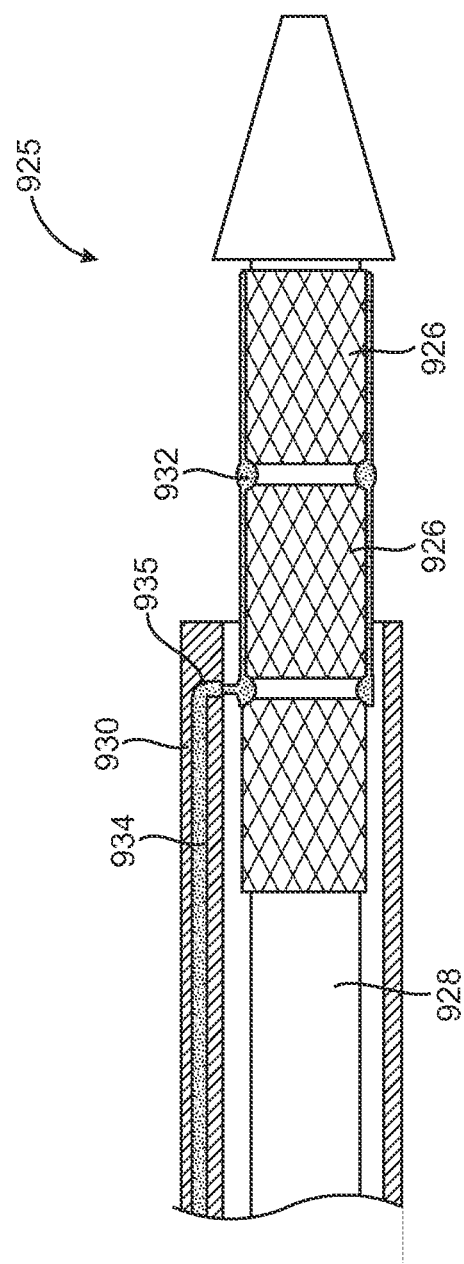
FIGS. 15A-15B show a liquid bonding material used to create a coupling structure between stent segments.
Figure 15B:
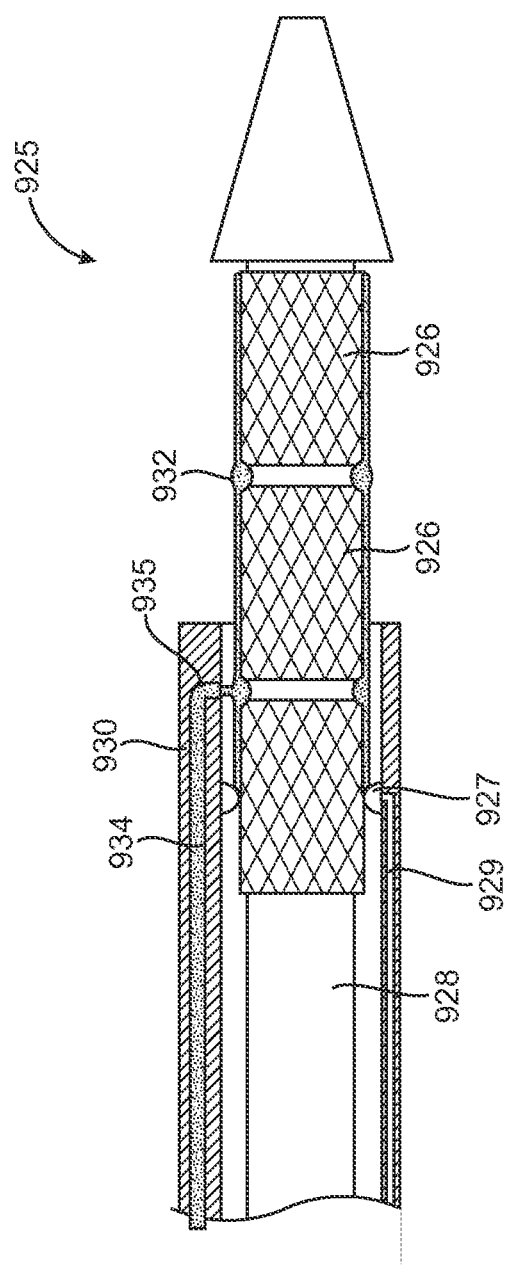

A liquid bonding material may also be delivered to stent segments selected for delivery as they are deployed. In FIG. 15A, a luminal prosthesis delivery system 925 has stent segments 926 disposed on a delivery catheter 928. As the stent segments 926 are exposed for delivery by retracting outer sheath 930, a liquid bonding material is applied to the stent segments 926 forming a coating layer or bead 932 which couples the stent segments 926 together. The liquid bonding material, maybe polylactic acid or another suitable polymer or other material, preferably bioedrodable, including SIBS, PEVA and PBMA. The liquid bonding material is dispensed via a lumen 934 in the delivery catheter outer sheath 930. An exit port 935 near the distal end of outer sheath 930 permits the liquid bonding material to be delivered to the stent segments 926 as they pass through the distal end of outer sheath 930. In alternative embodiments, delivery system 925 may be used to deliver a dissolving agent to stent segments that are bonded together thereby decoupling selected stent segments from one another. In still other embodiments, a valve member may be employed to prevent the bonding material or dissolving agent from moving proximally under sheath 930. In FIG. 15B, a valve member 927 is disposed on the inner surface of sheath 930 near its distal end. Valve member 927 may be an annular projection that is sized to close the gap between the inner surface of sheath 930 and the outer surface of stents 926. In some embodiments, the valve member 927 may be an inflatable balloon with a lumen 929 disposed in sheath 930.

Self-expanding links may be utilized as a coupling structure as shown in FIG. 16A. Here, a luminal prosthesis 950 is composed of a series of balloon-expandable stent segments 952 with self-expanding connection rings 954 therebetween. The connecting rings 954 are typically made from nitinol or other resilient or shape memory material which self-expands when released or unconstrained so the connecting rings expand along with balloon-expandable segments 952. Connecting hooks 956 couple connection rings 954 with the adjacent stent segment ends, forming an attachment therebetween. The self-expanding rings may be integrally formed on one end of balloon expandable segments 952, or the connecting rings may be attached at both ends to the adjacent stent segments by hooks 956, loops 980, or other suitable couplings. Hooks 956 or loops 980 may be decoupled by differential expansion of the stent segments, or may be a thermal shape memory alloy which forms a coupling or decouples when heated. Alternatively, the couplings may be a material which can be severed by a cutting mechanism on the delivery catheter.

FIG. 16C shows a lengthy luminal prosthesis 985 axially arranged on a delivery catheter 987 with an outer sheath 990. Here, balloon expandable stent segments 988 alternate with self-expanding stent segments 986 and hook-like coupling links 992 couple adjacent stent segments together. The coupling links 992 comprise loops which are sheared by differential expansion of adjacent stent segments, severed by means of a cutting mechanism on the delivery system or they may comprise hooks which can be disengaged by exerting sufficient axial tensile force or radial force on the attached stent segments.

Figure 17A:
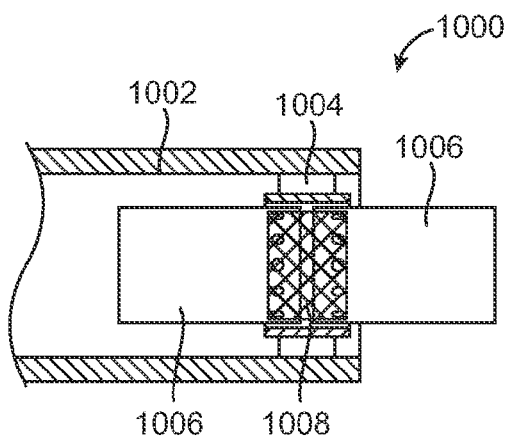
FIG. 17A shows a heating element used to decouple adjacent stent segments from one another.
Figure 17B:
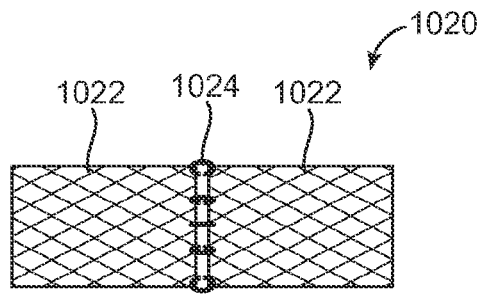
FIG. 17B shows adjacent stent segments coupled together with a thermal shape memory alloy or polymer coupling element.
Figure 17C:
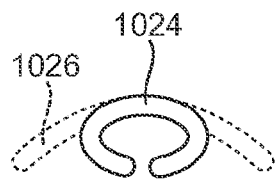
FIGS. 17C-17D show alternative geometries of thermal shape memory alloy coupling elements.
Figure 17D:
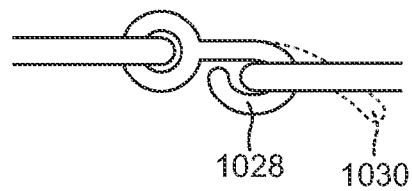
Figure 17E:
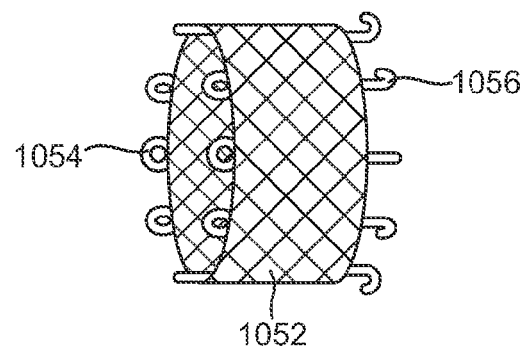
FIG. 17E shows a stent segment with thermal shape memory loops and hooks.

FIG. 17A further illustrates how thermal shape memory links may be used as coupling elements. The distal end of a luminal prosthesis delivery system 1000 is shown in FIG. 17A. Stent segments 1006 are coupled together with a thermal shape memory coupling element 1008. A heating element 1004 is disposed on outer sheath 1002. The coupling element 1008 may be heated by the heating element 1004 causing the coupling element to deform thereby releasing the adjacent stent segments 1006 from one another. The coupling element may be adapted to overlap around the exterior of the adjacent stent segments 1006, in which case the coupling element 1008 is adapted to increase its diameter upon heating to release the stent segments 1006. Alternatively, the coupling element 1008 may be adapted for placement inside the adjacent stent segments 1006, in which case heating the coupling element 1008 reduces its diameter to release stent segments 1006. In FIG. 17B adjacent stent segments 1022 are coupled together with C-shaped thermal shape memory coupling elements 1024. When heated, the coupling elements 1024 deform to an open position 1026 as shown in FIG. 17C. Other geometries are possible, such as that shown in FIG. 17D, where a hook-shaped coupling element 1028 also deforms to an open position 1030 when heated. Thermal shape memory hooks may be integrated onto each stent segment as shown in FIG. 17E, where each stent segment 1052 has a hook element on one end 1056 and a mating loop 1054 on the other end. Alternatively, the shape memory hooks may be disposed on connecting rings disposed between each balloon expandable segment, like those show in FIGS. 16A-C.

In another embodiment, and now with reference to FIG. 18, a luminal prosthesis delivery system 1100 is shown. Multiple stent segments 1102 are disposed on a delivery catheter balloon 1104 with an outer sheath 1108 in a retracted position to expose two stent segments 1102. In this embodiment, stent segments 1102 are initially unconnected to each other, and a coating or bead of adhesive 1106 is disposed on the end surfaces of each stent segment 1102. Following exposure of the desired number of stent segments 1102, heated fluid is introduced into the balloon via an inflation lumen 1110, thereby expanding the stent segments 1102 and simultaneously heating the adhesive or polymer 1106 between adjacent stent segments 1102. The heat melts the adhesive or polymer 1106 and it flows between adjacent stent segment ends bonding the segments together. In an alternative embodiment, the stent segments 1102 are initially bonded together by adhesive 1106. After the desired number of stent segments has been exposed, heated fluid is introduced into the balloon to cause the adhesive to at least partially liquefy but not yet fully expanding the balloon. The exposed stent segments may now be separated from those to remain on the delivery catheter by further retraction of the outer sheath, as described elsewhere in this application. Cooler fluid may then be introduced into the balloon to fully expand the exposed segments, which remain bonded together by the adhesive.

While the above is a complete description of the preferred embodiments of the invention, various alternatives, modifications, additions, and substitutions are possible without departing from the scope thereof, which is defined by the claims.

What is claimed is:

1. A luminal prosthesis comprising:
   a plurality of radially expandable prosthetic stent segments arranged axially, wherein a radially expandable prosthetic stent segment or group of radially expandable prosthetic stent segments of the plurality of radially expandable prosthetic stent segments is separable upon expansion from an adjacent radially expandable prosthetic stent segment of the plurality of radially expandable prosthetic stent segments, wherein each radially expandable prosthetic stent segment comprises distal and proximal ends with a wave pattern; and
   a separate coupling structure between each of the plurality of radially expandable prosthetic stent segments to couple and limit relative axial movement therebetween, wherein the separate coupling structure comprises a strand of flexible material that forms a plurality of loops that extend about the circumference of the luminal prosthesis, wherein the loops are formed by the strand of flexible material being threaded axially and circumferentially through openings in the radially expandable prosthetic stent segments such that each of the loops encircles at least two adjacent expandable prosthetic stent segment ends, and wherein each of the plurality of radially expandable prosthetic stent segments have a wall with openings therein, the strand of flexible material being threaded axially and circumferentially threaded about the entire circumference and through multiple openings in each of the radially expandable prosthetic stent segments, and wherein each opening in the plurality of radially expandable prosthetic stent segments is defined by a first curved side, a second curved side, a first straight side, and a second straight side, the first curved side couples to a first end of the first straight side and a first end of the second straight side, and the second curved side couples to a second end of the first straight side and to a second end of the second straight side, and wherein the first and second straight sides are spaced apart from each other;
   wherein severing the coupling structure permits the radially expandable prosthetic stent segment or a group of radially expandable prosthetic segments to separate from the adjacent radially expandable prosthetic stent segment of the plurality of radially expandable prosthetic stent segments upon differential radial expansion of the radially expandable prosthetic stent segment or the group of radially expandable prosthetic segments.

2. The luminal prosthesis of claim 1, wherein the flexible strand of material comprises a polymer thread.

3. The luminal prosthesis of claim 1, wherein the plurality of radially expandable prosthetic stent segments are arranged axially in an interleaving manner.

4. The luminal prosthesis of claim 1, wherein each of the radially expandable prosthetic stent segments comprises a first end and a second end wherein the first end comprises a first plurality of crests and troughs and the second end comprises a second plurality of crests and troughs.

5. The luminal prosthesis of claim 4, wherein the separate coupling structure couples the crests of the radially expandable prosthetic stent segments together.

6. The luminal prosthesis of claim 1, wherein the first and second straight sides are parallel to each other.

7. The luminal prosthesis of the claim 1, comprising third and fourth straight sides, wherein the third and fourth straight sides couple to peaks or troughs of the first and second curved sides.

8. The luminal prosthesis of claim 1, wherein the first curved side and the second curved side curve in a same direction such that the first curved side and the second curved side are parallel with one another.

9. The luminal prosthesis of claim 8, wherein each opening is formed by parallel first and second straight sides and parallel first and second curved sides.

10. A luminal prosthesis comprising:
    a plurality of radially expandable prosthetic stent segments arranged axially, wherein a radially expandable prosthetic stent segment or group of radially expandable prosthetic stent segments of the plurality of radially expandable prosthetic stent segments is separable upon expansion from an adjacent radially expandable prosthetic stent segment of the plurality of radially expandable prosthetic stent segments, wherein each radially expandable prosthetic stent segment comprises distal and proximal ends with a wave pattern; and
    a separate coupling structure between each of the plurality of radially expandable prosthetic stent segments to couple and limit relative axial movement therebetween, wherein the separate coupling structure comprises a strand of flexible material, and wherein each of the plurality of radially expandable prosthetic stent segments have a wall with openings therein, the strand of flexible material being threaded axially and circumferentially threaded about the entire circumference and through multiple openings in each of the radially expandable prosthetic stent segments, and wherein each opening in the plurality of radially expandable prosthetic stent segments is defined by a first curved side, a second curved side, a first straight side, and a second straight side, the first curved side couples to a first end of the first straight side and a first end of the second straight side, and the second curved side couples to a second end of the first straight side and to a second end of the second straight side, and wherein the first and second straight sides are spaced apart from each other, wherein the first curved side and the second curved side curve in a same direction such that the first curved side and the second curved side are parallel with one another such that each opening is formed by parallel first and second straight sides and parallel first and second curved sides;
    wherein severing the coupling structure permits the radially expandable prosthetic stent segment or a group of radially expandable prosthetic segments to separate from the adjacent radially expandable prosthetic stent segment of the plurality of radially expandable prosthetic stent segments upon differential radial expansion of the radially expandable prosthetic stent segment or the group of radially expandable prosthetic segments.

11. The luminal prosthesis of claim 10, wherein the strand of flexible material forms a plurality of loops that extend about the circumference of the luminal prosthesis, wherein the loops are formed by the strand of flexible material being threaded axially and circumferentially through openings in the radially expandable prosthetic stent segments such that each of the loops encircles at least two adjacent expandable prosthetic stent segment ends.

* * * * *